US012653445B2

(12) United States Patent
Robison et al.

(10) Patent No.: US 12,653,445 B2
(45) Date of Patent: Jun. 16, 2026

(54) AUGMENTED NEUROMODULATION AND BIOFEEDBACK FOR SYMPTOM INTERVENTION

(71) Applicant: Cionic, Inc., San Francisco, CA (US)

(72) Inventors: Jeremiah Robison, San Francisco, CA (US); Michael Dean Achelis, Walnut Creek, CA (US); Lina Avancini Colucci, Los Altos, CA (US); Sidney Rafael Primas, Los Altos, CA (US); Jonathan Sakai, Rocky River, OH (US); Andrew James Weitz, Bishop, CA (US)

(73) Assignee: Cionic, Inc., San Francisco, CA (US)

( * ) Notice: Subject to any disclaimer, the term of this patent is extended or adjusted under 35 U.S.C. 154(b) by 931 days.

(21) Appl. No.: 17/411,994

(22) Filed: Aug. 25, 2021

(65) Prior Publication Data

US 2022/0061741 A1 Mar. 3, 2022

Related U.S. Application Data

(60) Provisional application No. 63/071,376, filed on Aug. 28, 2020.

(51) Int. Cl.
*A61B 5/00* (2006.01)
*A61B 5/11* (2006.01)
(Continued)

(52) U.S. Cl.
CPC ............ *A61B 5/4082* (2013.01); *A61B 5/112* (2013.01); *A61B 5/251* (2021.01); *A61B 5/7267* (2013.01);
(Continued)

(58) Field of Classification Search
CPC ..... A61B 5/4082; A61B 5/112; A61B 5/1124; A61B 5/1101; A61B 5/7267; A61B 5/7275; G16H 50/20
See application file for complete search history.

(56) References Cited

U.S. PATENT DOCUMENTS 9,974,478 B1 * 5/2018 Brokaw ................. A61B 5/486
10,092,754 B1 10/2018 Heldman et al.
(Continued)

FOREIGN PATENT DOCUMENTS

WO WO 2018/152365 A1 8/2018
WO WO 2019/136110 A1 7/2019
WO WO 2020/069219 A1 4/2020

OTHER PUBLICATIONS

European Patent Office, Extended European Search Report and Written Opinion, Feb. 27, 2024, 9 pages.
(Continued)

*Primary Examiner* — Devin B Henson
(74) *Attorney, Agent, or Firm* — Fenwick & West LLP

(57) ABSTRACT

A symptom intervention system monitors data representative of a user's movement, identifies an onset of a symptom of a physical condition, and applies an actuation to intervene with the identified onset. A machine-learned model is trained to identify an onset of a symptom based on the monitored data. The system may use the machine-learned model to determine whether to modify an upcoming administration of a chemical stimulus that is administered to the user to treat their physical condition. The system may determine a modification to a dose or a time associated with the upcoming administration of the stimulus and apply the stimulus to the user based on the determined modification. The system may use the machine-learned model to determine that the user is exhibiting a particular symptom of their physical condition.

(Continued)

Depending on the symptom, the system may depolarize or hyperpolarize neurons of the user.

19 Claims, 11 Drawing Sheets

(51) Int. Cl.

| | |
|---|---|
| A61B 5/251 | (2021.01) |
| A61M 5/172 | (2006.01) |
| A61P 25/16 | (2006.01) |
| G06N 20/00 | (2019.01) |
| G06T 7/00 | (2017.01) |
| G06V 40/10 | (2022.01) |
| G06V 40/20 | (2022.01) |
| G16H 50/20 | (2018.01) |

(52) U.S. Cl.
CPC ......... *A61B 5/7275* (2013.01); *A61M 5/1723* (2013.01); *A61P 25/16* (2018.01); *G06N 20/00* (2019.01); *G06T 7/0012* (2013.01); *G06V 40/10* (2022.01); *G06V 40/20* (2022.01); *G16H 50/20* (2018.01); *A61M 2205/3303* (2013.01); *A61M 2205/50* (2013.01); *A61M 2205/502* (2013.01); *A61M 2230/06* (2013.01); *A61M 2230/08* (2013.01); *A61M 2230/42* (2013.01); *A61M 2230/62* (2013.01); *A61M 2230/63* (2013.01); *G06T 2207/30004* (2013.01); *G06T 2207/30196* (2013.01); *G06V 2201/03* (2022.01)

(56) References Cited

U.S. PATENT DOCUMENTS

| | | | |
|---|---|---|---|
| 10,744,324 B2 | 8/2020 | OLaighin et al. | |
| 2005/0277911 A1 | 12/2005 | Stewart et al. | |
| 2016/0106344 A1 | 4/2016 | Nazari | |
| 2017/0095670 A1* | 4/2017 | Ghaffari | A61M 21/02 |
| 2018/0206775 A1* | 7/2018 | Saria | A61B 5/6898 |
| 2018/0353698 A1 | 12/2018 | Saint et al. | |
| 2018/0361153 A1 | 12/2018 | Heldman et al. | |
| 2019/0043610 A1 | 2/2019 | Vaughan | |
| 2019/0069815 A1 | 3/2019 | Burnes et al. | |
| 2019/0365286 A1* | 12/2019 | Powers, III | A61B 5/6828 |
| 2020/0155078 A1 | 5/2020 | Mei et al. | |
| 2021/0402172 A1* | 12/2021 | Ross | A61H 1/00 |
| 2022/0031194 A1* | 2/2022 | Ong | A61B 5/4836 |
| 2022/0175555 A1 | 6/2022 | Robison et al. | |
| 2022/0176545 A1 | 6/2022 | Robison et al. | |
| 2023/0039154 A1 | 2/2023 | Robison et al. | |
| 2023/0045403 A1 | 2/2023 | Robison et al. | |

OTHER PUBLICATIONS

PCT International Search Report and Written Opinion, PCT Application No. PCT/US2021/47592, Dec. 17, 2021, 40 pages.
United States Office Action, U.S. Appl. No. 17/411,968, filed Dec. 18, 2024, 31 pages.
European Patent Office, Extended European Search Report, European Patent Application No. Application Number 25214196, dated Jan. 23, 2026, 9 pages.

* cited by examiner

100

Symptom Intervention
Assembly
110

400

800

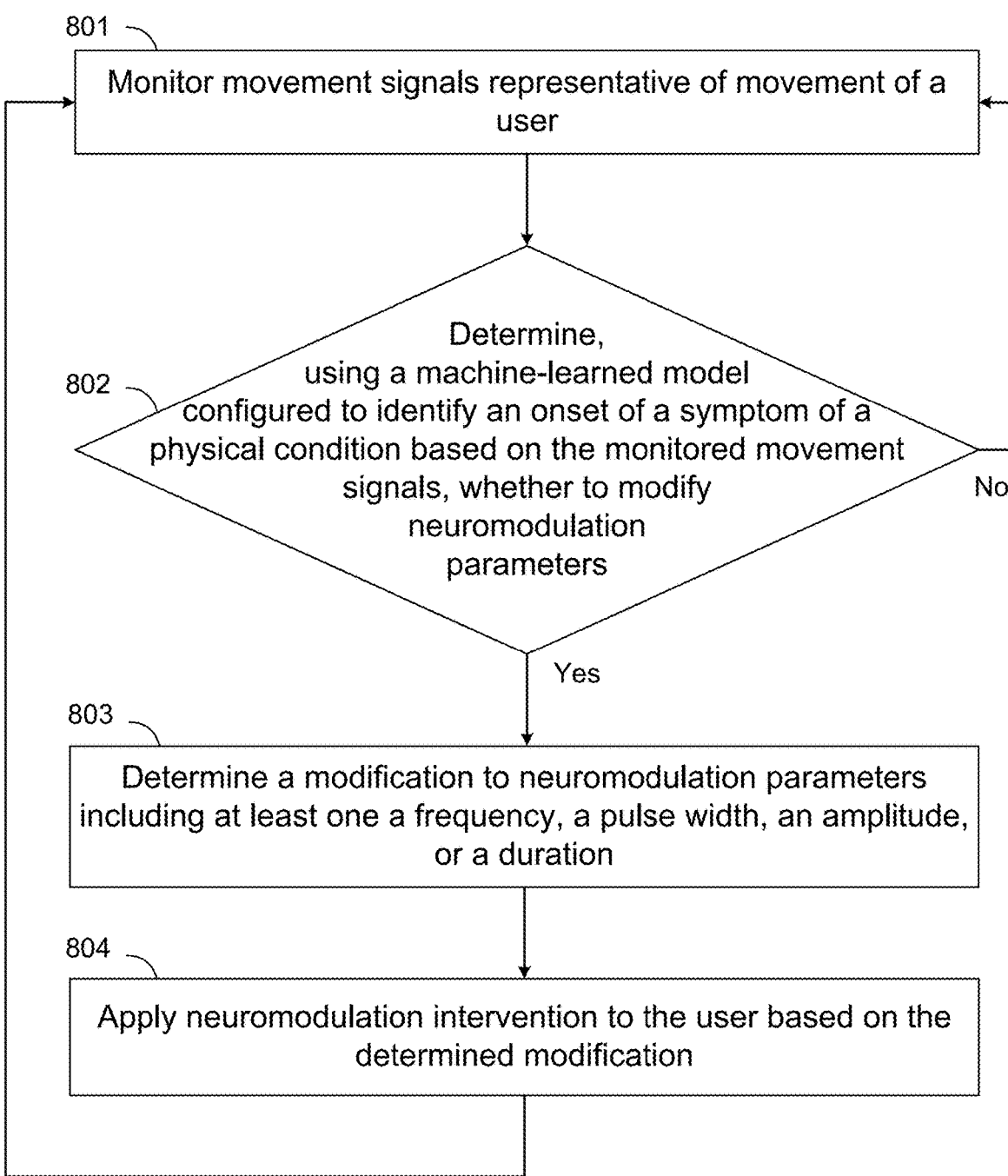

801

Monitor movement signals representative of movement of a user

802

Determine, using a machine-learned model configured to identify an onset of a symptom of a physical condition based on the monitored movement signals, whether to modify neuromodulation parameters No Yes

803

Determine a modification to neuromodulation parameters including at least one a frequency, a pulse width, an amplitude, or a duration

804

Apply neuromodulation intervention to the user based on the determined modification

FIG. 8

1000
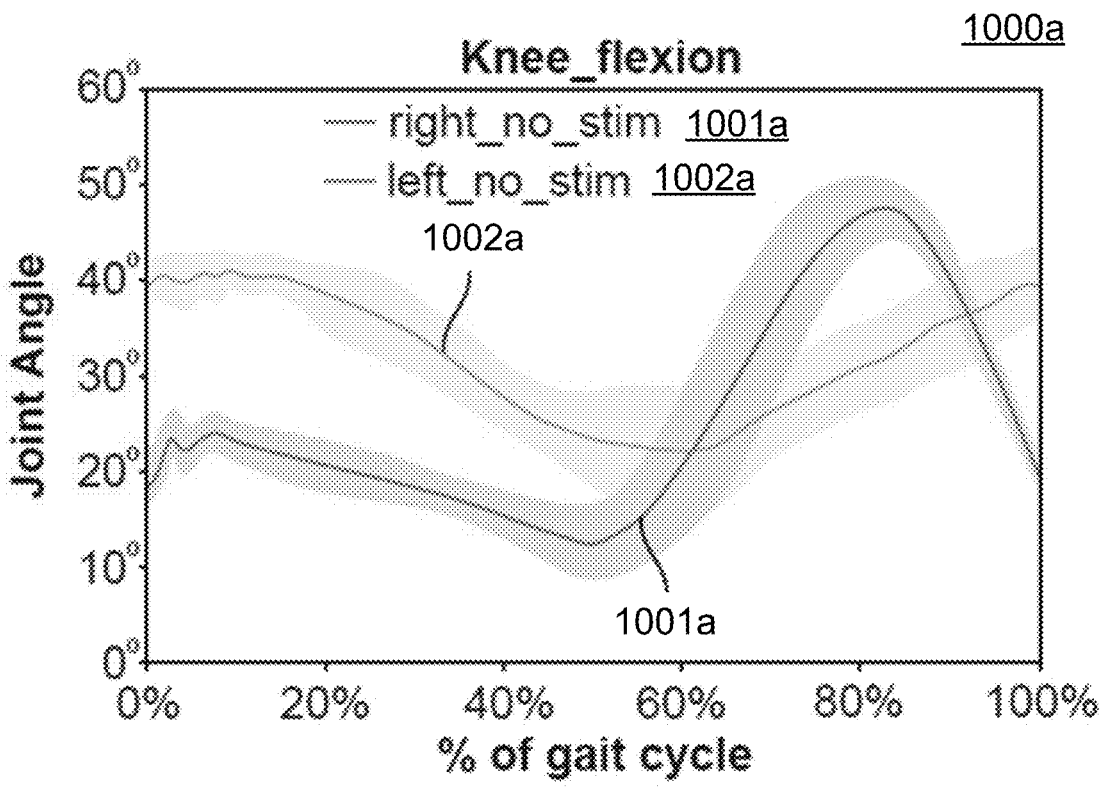
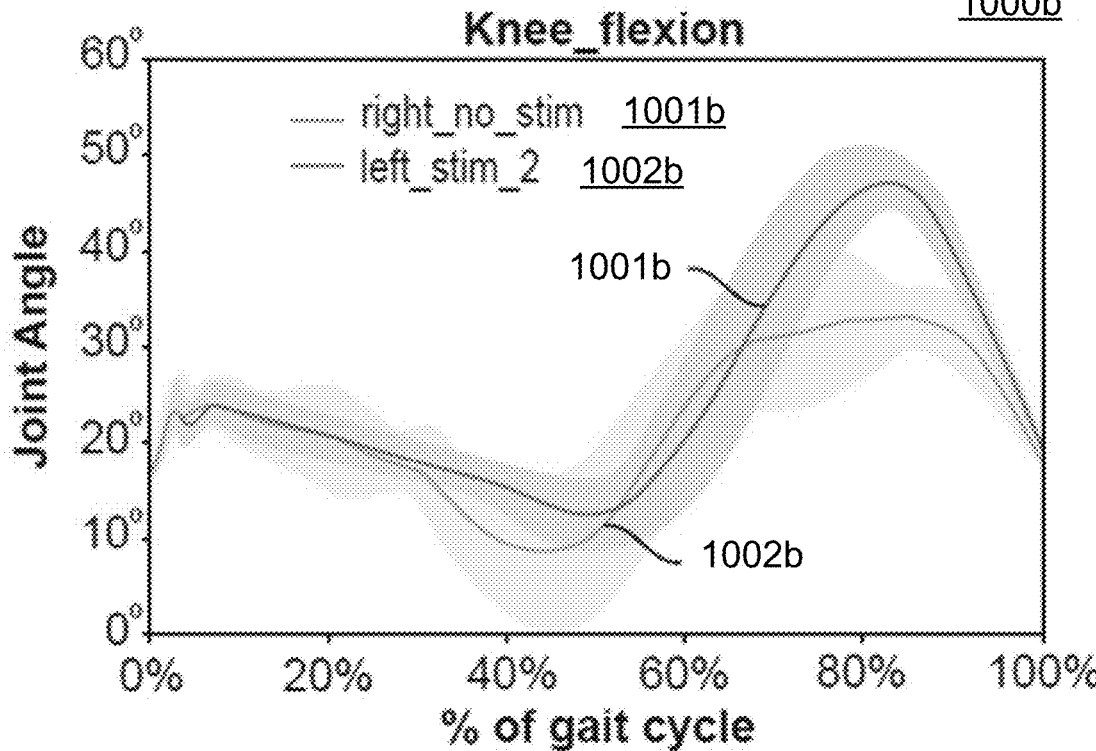
FIG. 10

1100

1200
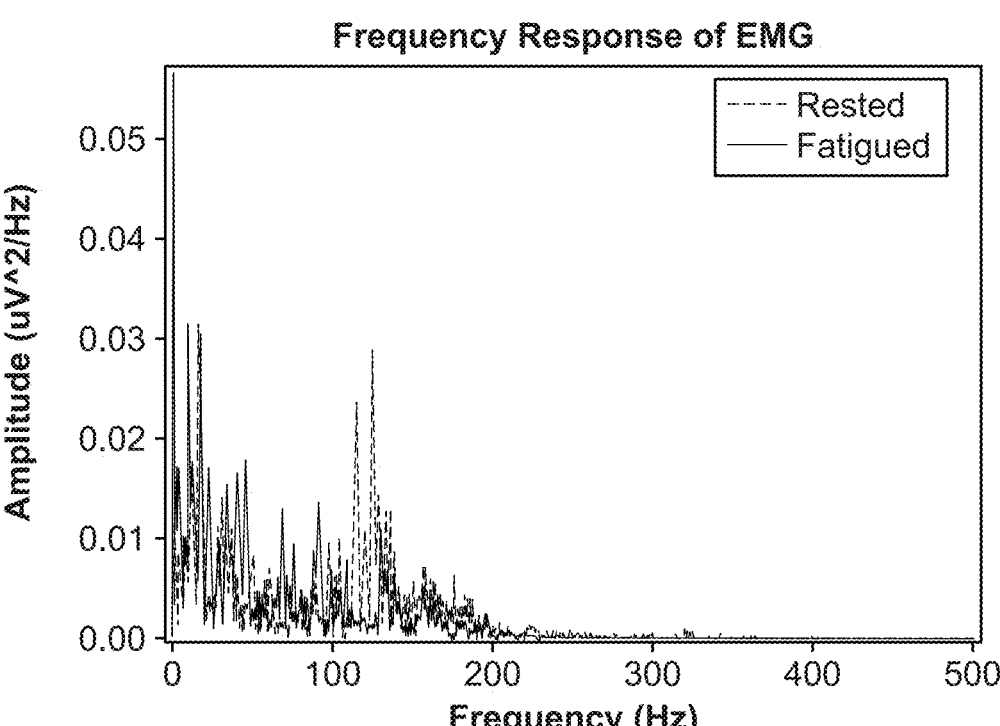
1210
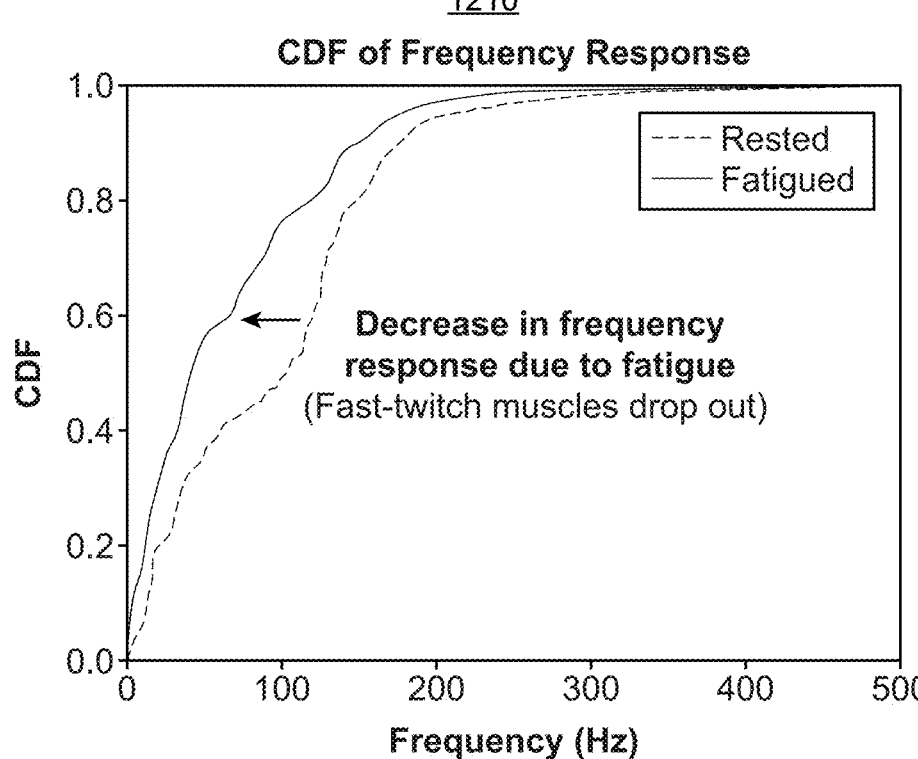
FIG. 12

AUGMENTED NEUROMODULATION AND BIOFEEDBACK FOR SYMPTOM INTERVENTION

CROSS REFERENCE To RELATED APPLICATIONS

This application claims the benefit of U.S. Provisional Application No. 63/071,376, filed Aug. 28, 2020, which is incorporated by reference in its entirety.

TECHNICAL FIELD

This disclosure relates generally to a symptom intervention system, and more specifically to monitoring of activity of a user (e.g., motor activity) and optimizing symptom intervention based on the monitored activity.

BACKGROUND

Conditions such as cerebral palsy, multiple sclerosis, and Parkinson's disease have undesired effects on motor function and are yet to be curable. For example, Parkinson's disease (PD) is the second most common neurodegenerative disorder, affecting 10 million people worldwide. Characterized by tremor, muscular rigidity, and decreased mobility, PD has a staggering effect on quality of life and leaves many patients unable to walk or feed themselves. The economic burden of PD is also significant, reaching over $25 billion in direct medical costs ($50 billion total) in the United States. While the neurobiology of Parkinson's disease and its characteristic loss of dopamine-producing neurons is well described, the disease remains incurable. Existing treatments to conditions such as PD fail to stop disease progression, are challenging to titrate, and have themselves several undesirable motor side effects.

Chemical stimuli can help care for patients with such conditions. For example, oral administration of levodopa (l-DOPA) is one manner of care for PD. As a precursor to dopamine, l-DOPA reverses the chemical imbalance caused by Parkinson's and, in turn, restores normal motor function. However, achieving its proper dosage remains a major challenge. When l-DOPA levels in the bloodstream become low, symptoms of motor dysfunction can return without notice ("off" periods). Conversely, high levels can lead to visual hallucinations and involuntary movements. This titration becomes further complicated as the disease progresses and more neurons in the brain die. The general unpredictability of a patient's symptoms over the course of a day can lead to secondary issues such as anxiety, depression, and isolation that results from avoiding social interactions.

Although these conditions can be marked by a handful of hallmark characteristics, each are highly variable and no two patients having the same condition will exhibit the same combination or degree of symptoms. Clinicians therefore rely on standardized rating scales to assess a patient's condition, track disease progression, and evaluate responsiveness to treatment. For example, the motor section of the Unified Parkinson's Disease Rating Scale (UPDRS), which is the gold standard for assessing a PD patient's motor symptoms, requires the patient to perform a series of motor tasks, which are visually evaluated by trained personnel. Unfortunately, these rating scales are limited by poor temporal resolution and the subjective nature of scoring. Because symptom severity fluctuates through the day and can worsen with multitasking, clinical exams are also unlikely to capture the real-world severity of a patient's disease.

SUMMARY

The symptom intervention methods and systems described herein implements machine learning and control mechanisms to personalize and optimize a user's management of physical condition symptoms. A symptom intervention assembly addresses the challenges with chemical stimuli titration in managing the symptoms of physical conditions by supplementing the chemical stimuli with a device-led combination therapy that increases the precision in which the stimuli is titrated and helps restore a patient's ability to perform otherwise difficult activities. The assembly can perform closed-loop monitoring and augmentation of motor activity. On-body sensors provide continuous measurements of symptom state and applies an actuation that intervenes with symptoms of a physical condition. For example, the assembly can stimulate the neuromuscular system to directly augment movements and improve mobility through neuromodulation or functional electrical stimulation (FES).

The symptom intervention assembly described herein determines an actuation to intervene with an onset of a physical condition's symptom using a machine-learned model that identifies the onset of the symptom based on monitored activity data such as muscle kinematics, muscle electroactivity, hormone levels, and chemical stimuli intake. The machine-learned model can be trained on generalized activity data collected across a population of users or on data associated with a particular user's activity, which fine tunes its symptom onset identification for that user and enables personalized symptom intervention. The assembly uses the identified onset to determine an actuation instruction for intervening with the symptom. The actuation instruction can also be personalized to a user.

After the symptom intervention assembly applies an actuation instruction, the assembly can monitor the user's movement to gauge a level of efficacy of the applied actuation in intervening with the identified symptom onset. By comparing the monitored movement to a target movement (e.g., a neurotypical gait or stillness of a hand that is not experiencing a tremor), the system can re-train the machine-learned model and further personalize the actuation to the user.

In one embodiment, a symptom intervention system identifies a chemical stimulus administered to a user to treat a physical condition of a user. An upcoming administration of the chemical stimulus is characterized by at least one of a dose and a time to administer the chemical stimulus.

The system monitors movement signals representative of movement of the user. For example, the system monitors inertial measurement unit (IMU) signals taken as the user is walking. The system determines, using a machine-learned model configured to identify an onset of a symptom of the physical condition based on the monitored movement signals, whether to modify the upcoming administration of the chemical stimulus. The monitored signals may, for example, show that the user is experiencing a slowing or shuffling gait. In response to determining to modify the upcoming administration of the chemical stimulus, the system determines a modification to the dose or the time associated with the upcoming administration of the chemical stimulus and applies the chemical stimulus to the user based on the determined modification. For example, the system may administer an increased dose of levodopa to the user or administer the upcoming dose of levodopa earlier than scheduled.

The symptom intervention system can train the machine-learned model using historical activity data, which can be collected across a population of users. The system can receive historical activity data collected from sensors configured to monitor a given user's activity data, where the historical activity data includes at least one of historical movement signals, hormone activity, a previous administration of the chemical stimulus, a heart rate, or a respiration rate. The system labels the historical activity data with a given symptom label representative of a corresponding symptom characterized by the historical activity data, creates a first training set based on the labeled historical activity data, and trains the machine-learned model using the first training set.

The system can label the monitored movement signals with a symptom label representative of the symptom characterized by the monitored movement signals, create a second training set using the labeled movement signals, and retrain the machine-learned model using the second training set such that the machine-learned model is customized to the motions of the user. The system can also receive feedback of the determined modification indicating a measure of approval that the user has with the determined modification, modify an association between the identified onset of the symptom of the physical condition and the monitored movement signals, and retrain the machine-learned model using the modified association.

Hormone activity of the user can be monitored by the system using sensors configured to measure at least one of a level of a hormone or a level of a biomolecule regulated by the hormone. The machine-learned model may be configured to identify the onset of the symptom of the physical condition further based on the monitored hormone activity. The system can determine whether to modify the upcoming administration of the chemical stimulus by generating a feature vector representative of the monitored movement signals and one or more of a hormone activity of the user, a previous administration of the chemical stimulus, and motor intent data of the user. The machine-learned model can be applied to the feature vector, where the machine-learned model identifies the onset of the symptom with a confidence score as being associated with the feature vector. In response to the confidence score exceeding a threshold confidence, the system can determine to modify the upcoming administration of the chemical stimulus.

In some embodiments, the system may determine an "on" time duration of a previous administration of the chemical stimulus. The "on" time duration can start at a first time to administer the chemical stimulus and end at an occurrence of the symptom after the first time to administer the chemical stimulus. The system can identify the first occurrence of the symptom using the machine-learned model. The system may also determine an "off" time duration of the previous administration of the chemical stimulus. The "off" time duration can start at the first occurrence of the symptom and end at a second time to administer the chemical stimulus after the first time. The system can determine whether to modify the upcoming administration of the chemical stimulus by determining if the "off" time duration is greater than the "on" time duration and, if so, determine to modify the upcoming administration.

The system can cause a client device to render a graphical user interface (GUI) including user input fields to approve or reject the determined modification. In response to receiving a user input indicating that the determined modification is approved, the system can modify the dose or the time associated with the upcoming administration of the chemical stimulus. Similarly, the system can cause a client device to render a GUI including a user input field to stop a neuromodulation of the first group of neurons. In response to receiving a user input at the user input field, the system may modify an association between the identified onset of the symptom of the physical condition and the monitored plurality of movement signals. The system can retrain the machine-learned model using the modified association.

In some embodiments, the system can determine kinematic metric scores to identify the symptom onset. The system measures movement signals at two joints of the user, where the two joints are symmetric to one another about the sagittal plane. The system can determine a first kinematic metric score based on a comparison of the movement signals of one joint to the movement signals of the other, where the first kinematic metric score indicates a measure of symmetry of motion about the sagittal plane. A baseline movement profile of one joint can be generated by the system using historical movement signals collected at that joint. The system can determine a second kinematic metric score based on a comparison of the movement signals of the other joint to the baseline movement profile, where the second kinematic metric score indicates a measure of a variance from an expected movement. The machine-learned model may be configured to identify the onset of the symptom of the physical condition further based on at least one of the first kinematic metric score or the second kinematic metric score.

The system can determine a frequency response of the movement signals. The machine-learned model can be configured to identify the onset of the symptom of the physical condition further based on this movement frequency response. The system can measure movement signals at a muscle group of a foot, a shank, or a thigh of the user, where the movement signals represent a phase in a gait cycle. The system may create a baseline gait profile using historical movement signals measured at the muscle group. A gait report score can be determined by the system based on a comparison of the movement signals to the baseline gait profile. The machine-learned model may be configured to identify the onset of the symptom of the physical condition further based on the gait report score.

The modification to the dose or the time associated with the upcoming administration of the chemical stimulus can be based on a comparison of movement signals to a symptom profile, where the movement signals represent a symptom-affected movement of the user. The system may monitor the movement signals and compare them to the symptom profile created using historical movement data representative of movement while a given user is experiencing the symptom without assistance from chemical stimulus. In some embodiments, the system may determine a change in user posture depicted in images received from a camera, and the machine-learned model may be configured to identify the onset of the symptom of the physical condition further based on the change in user posture.

In some embodiments, motor intent data of the user can be monitored by the symptom intervention system. The motor intent data can include electromyography (EMG) signals. The system can determine a frequency response of the motor intent data, where the frequency response is indicative of an energy of muscle activity of the user, and determine a measure of fatigue based on a comparison of the frequency response and a rested frequency response profile determined using historical EMG signals. The machine-learned model can be configured to identify the onset of the symptom of the physical condition further based on the measure of fatigue.

The system may, in response to determining to modify the upcoming administration of the chemical stimulus, provide biofeedback to the user. The biofeedback can include one or more of a sensory cue (e.g., visual, audio, or haptic) to promote a neurotypical movement in the user. In some embodiments, the system can identify a stimulus metabolism period indicating a time period between the intake of the chemical stimulus and a peak efficacy of the chemical stimulus. The system can determine to modify the time to administer the chemical stimulus, which can be referred to as an administration time, by determining a time at which an "off" time duration of the chemical stimulus will begin and updating the administration time to be earlier, by the stimulus metabolism period, than the time at which an "off" time duration of the chemical stimulus will begin.

The physical condition can be Parkinson's disease and the symptom is either a gait freeze, or freeze of gait (FOG), or a tremor. The chemical stimulus can be one of levodopa, carbidopa, or baclofen. In some embodiments, the physical condition is cerebral palsy and the symptom is crouch gait.

In another embodiment, a symptom intervention system applies a neuromodulation operation to intervene with a symptom of a physical condition. The system monitors movement signals representative of movement of a user. For example, the system can monitor kinetic or EMG signals captured as the user is walking or standing. The system can determine, using a machine-learned model configured to identify an onset of a symptom of a physical condition based the monitored movement signals, that the user is exhibiting a symptom of the symptoms of the physical condition. The system can, for example, determine whether the user is experiencing a slowed gait while walking or a tremor while standing. Based on a magnitude of the symptom exhibited by the user and characteristics of the user, the system can identify a neuromodulation operation to mitigate the symptom. For example, the neuromodulation operation can be identified based on a deceleration of a slowed gait or the acceleration of the user's shaking hands. The neuromodulation is also identified based on characteristics of the user, which can include historical records of applied neuromodulation or feedback related to their efficacy. The system applies the identified neuromodulation operation to the user via a wearable neuromodulation system, which includes electrodes coupled to the user.

The system can identify a neuromodulation operation depending on the symptom identified. In response to determining that the symptom is a first symptom of the physical condition's symptoms, the system can depolarize a first group of neurons of the user. For example, if the user is experiencing a slowed gait, the system depolarizes neurons to cause muscles to contract. In response to determining that the symptom is a second symptom of the physical condition's symptoms, the system can hyperpolarize a second group of neurons of the user. For example, if the user is experiencing a tremor, the system hyperpolarizes neurons to cause muscles to relax.

The system may depolarize the first group of neurons by determining at least one of a set of electrodes, which can be configurable to operate as either a cathode or anode, to operate as a cathode. The system may hyperpolarize the second group of neurons by determining at least another one of the set of configurable electrodes to operate as an anode. In some embodiments, the system compares the movement signals to a symptom profile that is created using historical movement data representative of movement while a given user is experiencing the symptom without assistance from a chemical stimulus. The system may depolarize the first group of neurons by determining electrical stimulation parameters based on the comparison of the movement signals to the symptom profile, the electrical stimulation parameters including a voltage or current amplitude, a pulse width, a polarity, or a frequency of an electrical stimulation signal. The electrical stimulation signal can be configured by the system to flow between a first electrode and a second electrode of the wearable neuromodulation system's electrodes.

In some embodiments, the system may determine a change in a frequency at which the onset of the symptom is identified. The first group of neurons can be depolarized by determining electrical stimulation parameters of an electrical stimulation signal based on the change in the frequency and configuring the electrical stimulation signal to flow between a first electrode and a second electrode.

BRIEF DESCRIPTION OF THE DRAWINGS

FIG. 8 is a flowchart illustrating a process for applying neuromodulation, in accordance with at least one embodiment.

FIG. 10 shows experimental findings of knee kinematics augmented with FES.

FIG. 12 shows experimental findings of the impact of fatigue upon muscle electroactivity.

The figures depict various embodiments for purposes of illustration only. One skilled in the art will readily recognize from the following discussion that alternative embodiments of the structures and methods illustrated herein may be employed without departing from the principles described herein.

DETAILED DESCRIPTION

System Architecture

Figure 1:
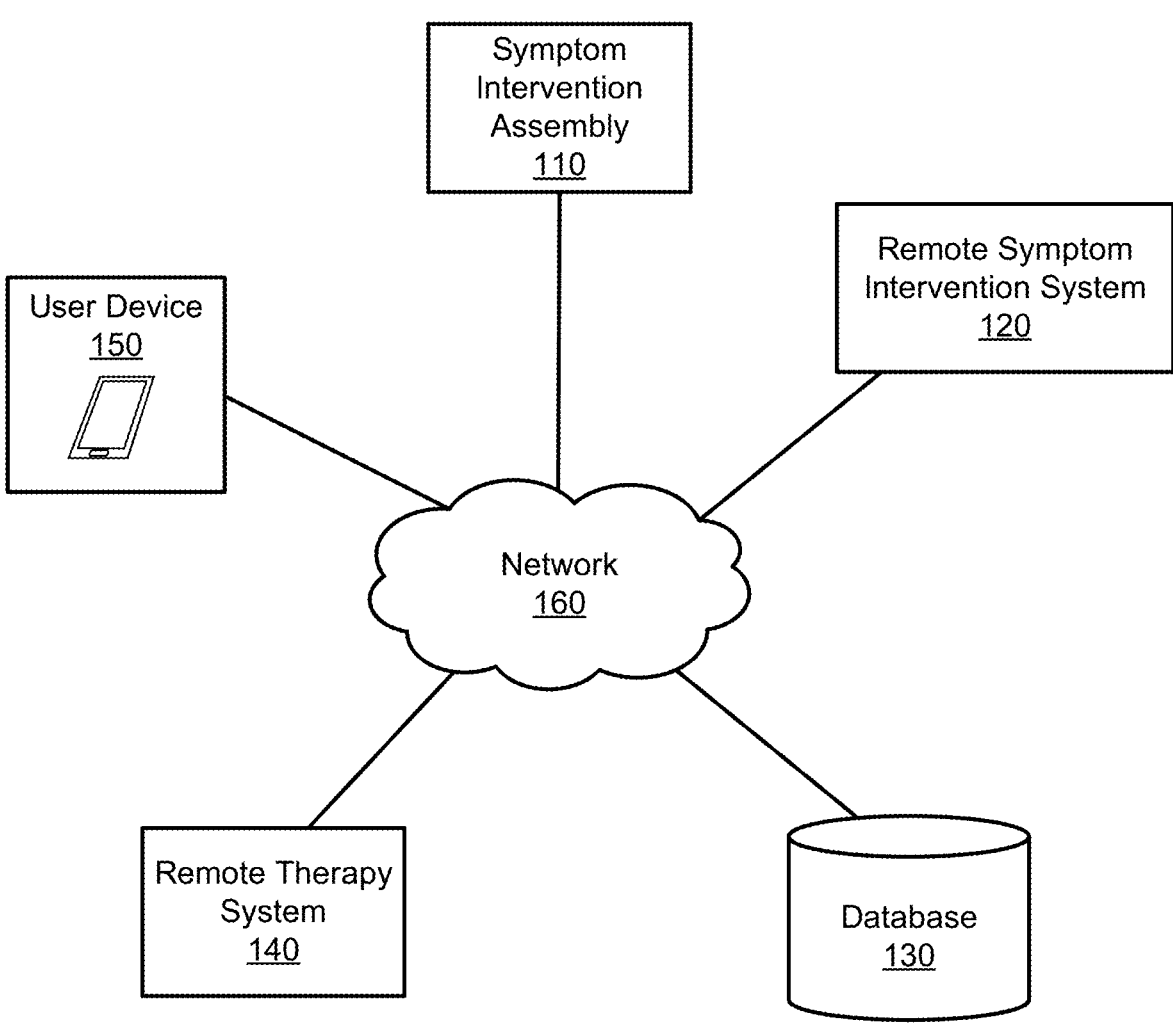
FIG. 1 is a block diagram of a system environment in which a symptom intervention assembly operates, in accordance with at least one embodiment.

FIG. 1 is a block diagram of a system environment 100 in which a symptom intervention assembly 110 operates. The system environment 100 includes the symptom intervention assembly 110, a remote symptom intervention system 120, a database 130, a remote therapy system 140, a user device 150, and a network 160. The system environment 100 may have alternative configurations than shown in FIG. 1, including for example different, fewer, or additional components. For example, a medical device delivering a chemical stimulus may be communicatively coupled with the network 160 to the symptom intervention assembly 110. In another example, the remote therapy system 140 may be omitted from the system environment 100 without compromising the functionality of the symptom intervention assembly 110.

The system environment 100 enables the symptom intervention assembly 110 to manage symptoms of its users' physical conditions. The symptom intervention assembly 110 may monitor the user's activity data for an onset of a symptom and apply actuation that intervenes with the symptom. For users of the symptom intervention assembly 110 with Parkinson's disease, the symptom intervention assembly 110 can identify an onset of a symptom of Parkinson's disease such as tremors, FOG, and bradykinesia.

As referred to herein, "activity data" may refer to data representative of activity of the user's body such as physical movement, electrical muscle activity, heart rate, respiration, hormone activity, administration of a chemical stimulus, or combination thereof. Activity data may include movement data such as kinetic, kinematic, pressure, or EMG signals. As referred to herein, the term "movement" may include stillness in addition to motion of a user's body unless context suggests otherwise. For example, a user's hand may be still and unmoving, as intended by the user, when the onset of a tremor begins and the user's hand begins to move. Here, stillness is an intended movement that can be monitored by the symptom intervention assembly 110 and the user's monitored movement is transitioning to movement affected by the tremor. The use of "symptom intervention" and "intervene with a symptom" herein may refer to the prevention, reduction in effect, or termination of an occurrence of a physical condition's symptom. Although the term "users" refer to human users, the systems and methods described herein may be similarly applied to augmenting movement for animals as well.

In one example, the assembly 110 identifies the onset of bradykinesia through monitored IMU signals capturing the user's slowing gait and applies neuromodulation to treat the slowed movement. The assembly 110 can also determine parameters of the neuromodulation to address the present characteristics of the user's slowing gait. That is, the assembly 110 can optimize actuation to address not only the symptom but the symptom as experienced by the user at the current moment, as not all patients of physical conditions experience their symptoms similarly. The assembly 110 can achieve this optimization through a feedback process.

In some embodiments, the symptom intervention assembly 110 may receive or monitor feedback of the applied actuation and modify subsequently applied actuation to optimize its treatment to the user. In the first example, the assembly 110 monitors IMU signals capturing the user's gait as the neuromodulation is applied. Using these monitored signals, the assembly 110 may determine to what extent the user's gait resembles a neurotypical gait or a baseline gait of the user when they are not experiencing their Parkinson's disease symptoms. This determination may serve as feedback for the assembly 110 to determine the efficacy of its applied neuromodulation and whether the neuromodulation should be adjusted for subsequent IMU signals that show a similar slowing gait.

In a second example, the assembly 110 identifies the onset of tremors through data representative of the efficacy of levodopa. In this example, the assembly 110 determines time periods during which levodopa, a chemical stimulus taken for Parkinson's disease, is effective ("on" period) and is diminished in effectiveness ("off" period). These periods can be determined through monitored data representative of the efficacy of a chemical stimulus such as a user's hormone activity and stimulus dosage (e.g., amount and timing). By determining whether the user is currently experiencing an "on" or "off" state of their chemical stimulus, the assembly 110 can identify a likelihood that an onset of a symptom will occur or when it will occur. Based on this identification, the assembly 110 can determine when to apply a chemical stimulus. In the second example, the assembly can cause a levodopa pump to deliver levodopa to the user so that the user is given enough time to metabolize the dose and stop the onset of the tremor. Thus, the assembly 110 can time symptom intervention to optimize the efficacy of a chemical stimulus with respect to the identified symptom.

Figure 2:
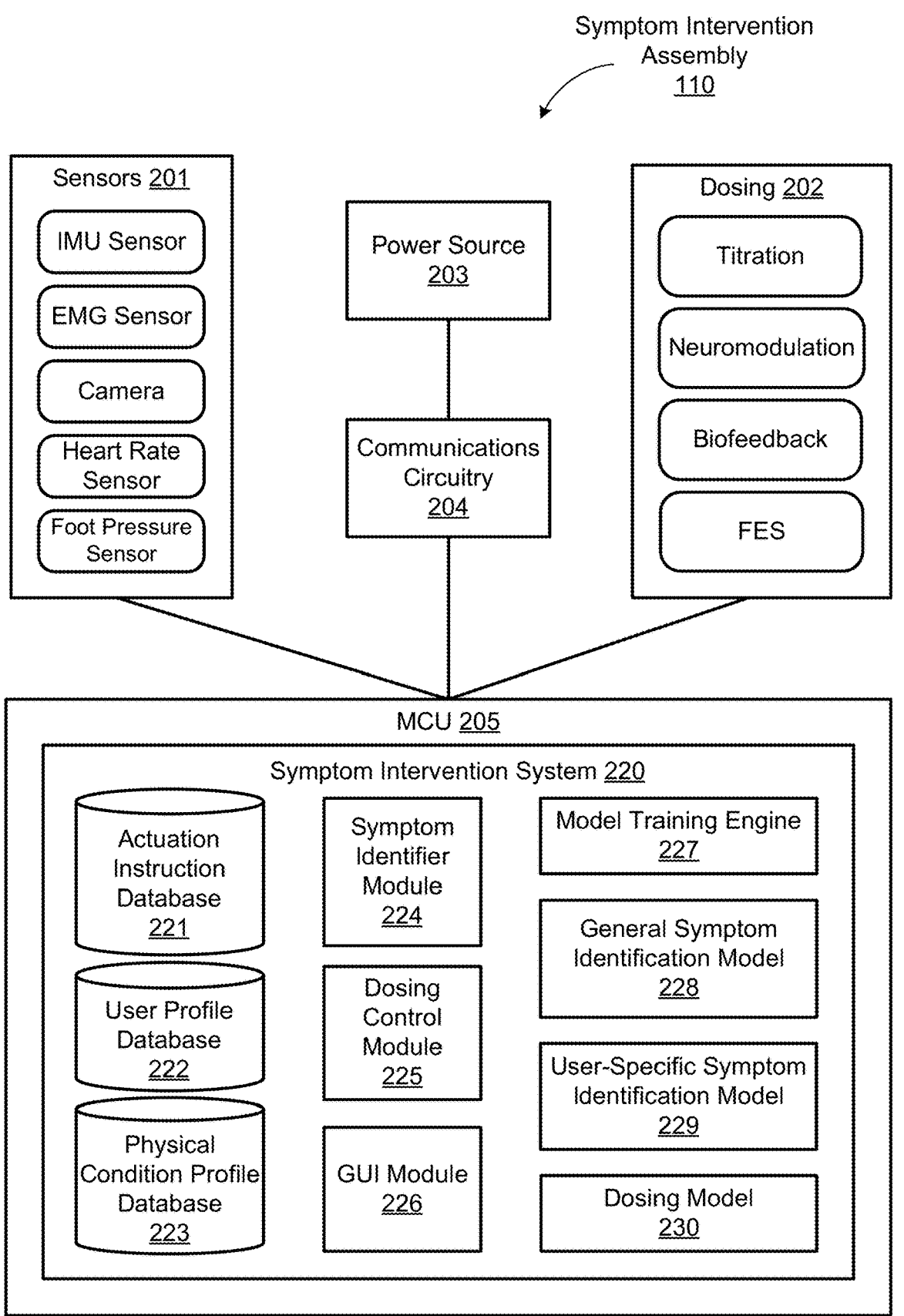
FIG. 2 is a block diagram of the symptom intervention assembly of FIG. 1, in accordance with at least one embodiment.

Additional details of how the symptom intervention assembly 110 identifies onsets of symptoms and determines an actuation to intervene with the identified onset are described in the description of FIG. 2. Furthermore, Parkinson's disease is a non-limiting example of a physical condition that the assembly 110 can help manage. The symptom intervention assembly 110 can intervene in symptoms of various physical conditions such as cerebral palsy (CP), multiple sclerosis (MS), having suffered from a stroke, or any suitable condition affecting the movement of a user.

The symptom intervention assembly 110 enables both personalization and optimization of symptom intervention for its users. One way in which the assembly 110 personalizes symptom intervention is by using activity data collected from the user to train a user-specific machine-learned model that is used in determining actuation instructions (e.g., neuromodulation parameters or an amount of a chemical stimulus delivered) for intervening with the user's subsequent symptoms. The assembly 110 may optimize symptom intervention by measuring the effectiveness of the actuation instructions in real time and varying subsequently applied actuation instructions based on the measurement. Achieving personalization and optimization using a symptom intervention system is described in further detail throughout the description FIGS. 2 and 3.

Figure 4:
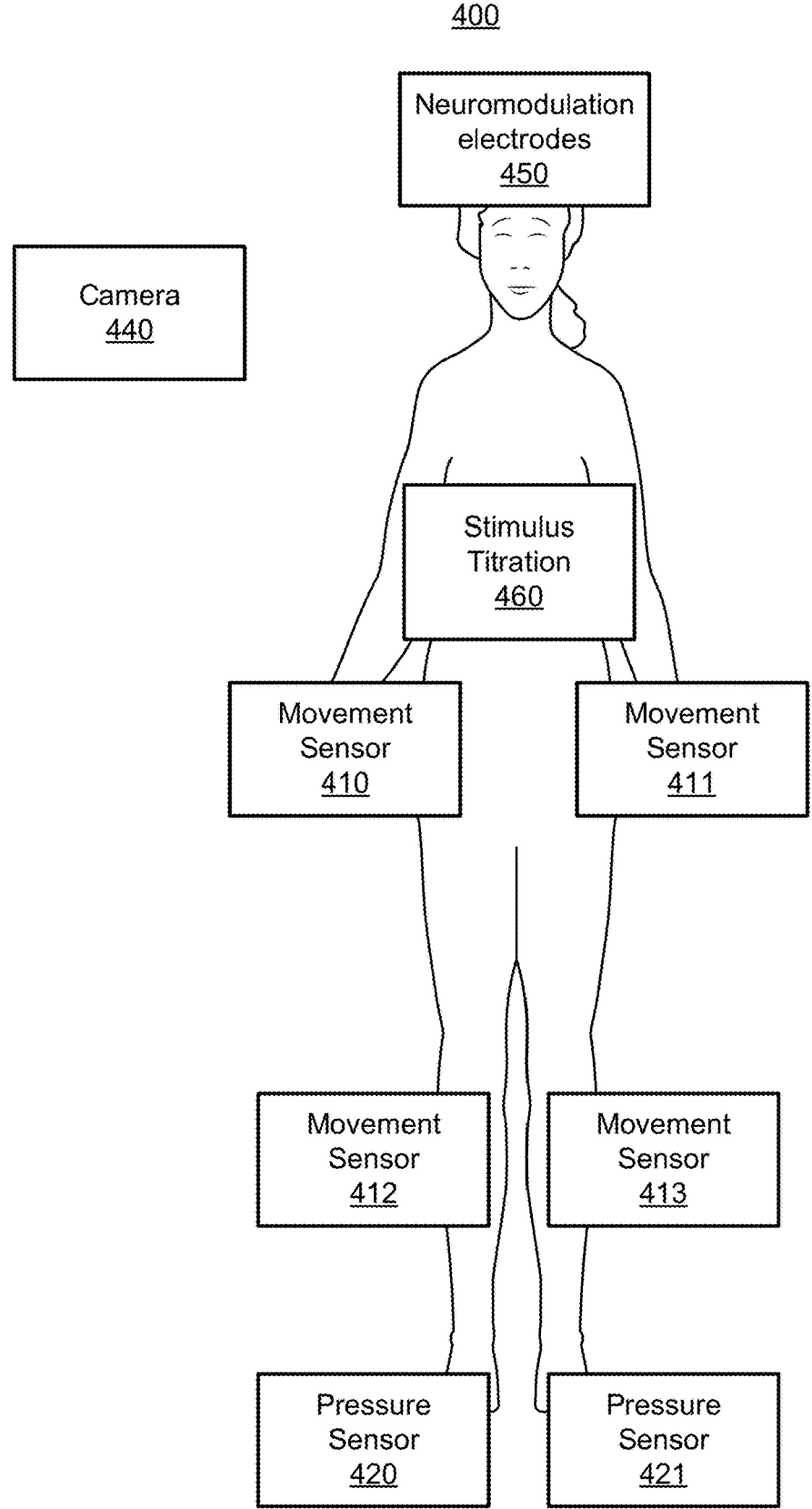
FIG. 4 shows a configuration of symptom intervention assembly components on or near a user's body, in accordance with at least one embodiment.

The symptom intervention assembly 110 may have various, wearable form factors such as exoskeletons, modular electrode straps, leggings, any wearable form factor suitable for targeting a particular muscle group on a user's body, or a combination thereof. The assembly 110 may include various components with different form factors that are communicatively coupled to one another. For example, the assembly 110 may include a legging that is worn underneath regular attire and is equipped with sensors and actuators for performing the symptom intervention described herein. The legging may be communicatively coupled to a wrist wrap or sleeve of the assembly 110 that is also equipped with sensors or actuators for symptom intervention at the wrist or arms (e.g., reducing tremors at the user's hands). The legging and sleeve may be further coupled to a neuromodulation device of the assembly 110 that is implanted within the user (e.g., a electrical wiring and electrodes embedded within the user to deliver deep brain stimulation (DBS) to the user's brain). An example configuration of some components of the assembly 110 is depicted in FIG. 4.

The remote symptom intervention system 120 receives and processes data from the symptom intervention assembly 110. The data received from the symptom intervention assembly 110 may include monitored activity data, identified symptoms, applied actuation instructions to intervene with identified symptoms, and feedback of the symptom intervention (e.g., user feedback). This data may be used to optimize symptom identification, generate new actuation instructions, or modify existing actuation instructions. The remote system 120 may use the processed data to provide actuation instructions for the assembly 110 to execute. The remote symptom intervention system 120 may have functionality similar to that of the symptom intervention system 220 described in FIG. 2. The remote system 120 may be hosted on a server or computing device (e.g., a smartphone) that communicates with the symptom intervention assembly 110 via the network 160.

In some embodiments, the remote symptom intervention system 120 trains and applies one or more machine-learned models configured to identify an onset of a physical condition's symptom based on monitored activity data. In one embodiment, the remote symptom intervention system 120 trains the models based on activity data collected by sensors onboard the symptom intervention assembly 110. The assembly 110 sends, via the network 160, activity data to the remote symptom intervention system 120 and leverages the trained machine learning models to receive, from the remote symptom intervention system 120, an identification of an onset of a symptom as output by the one or more models. The remote symptom intervention system 120 may maintain models that are generalized to movement across a population or customized to a particular user, activity type, any suitable phenotypic trait, or a combination thereof. The training and application of machine learning models used for symptom intervention is further described in the description of FIG. 2.

The database 130 stores various data for maintaining models of the symptom intervention assembly 110. The data may be used to create a statistical model or train a machine-learned model. The data stored in the training database 130 may include labeled or unlabeled activity data and associated onset of a symptom, labels associated with symptoms or physical conditions, or templates associated with sequences of muscle firings for given movements. The symptom intervention assembly 110 may access the stored data to maintain models of the symptom intervention system 220. The symptom intervention assembly 110 may provide its measured data or feedback to the database 130. The provided data may be organized in a data structure including the provided data, biographical information identifying the user or the user's phenotypic traits, and a label identifying the symptom associated with the provided data.

The remote therapy system 140 enables a third party to monitor the user's activity and symptom experiences (e.g., as identified by the symptom intervention assembly 110) and analyze the information to further assist the user with their symptom management. A third party can be a medical professional. For example, a doctor uses the remote therapy system 140 to monitor a user's movement and adjust an actuation instruction upon identifying that the patient's symptoms are not managed properly under the current actuation instruction being applied. The remote therapy system 140 may be a software module that the third party may execute on a computing device (e.g., a smartphone). In some embodiments, the remote therapy system 140 is a standalone device that may be communicatively coupled to the symptom intervention assembly 110 to manually adjust or generate actuation signals used to augment the user's motion (e.g., overriding the symptom intervention assembly 110). The remote therapy system 140 may include an input interface for the third party to specify parameters of an actuation instruction (e.g., the amplitude and frequency of FES signals) and when to apply them. In some embodiments, a third party is not in the medical community but can monitor the user's activity and symptoms to observe a progress of their physical condition, which may be relayed by that third party to a medical professional. For example, family member of the user or athletic coach can help the user track their symptoms remotely through the remote therapy system 140.

The remote therapy system 140 may provide actuation instructions to be applied by the mobility augmentation system 130. In some embodiments, a user of the remote therapy system 140 (e.g., a doctor) may specify when to apply neuromodulation and the electrode configuration of the symptom intervention assembly 110 through which the neuromodulation should be applied. For example, the doctor may specify how and when to stimulate a user's gait based on a video camera, which may be a sensor of the assembly 110 that is communicatively coupled to the remote therapy system 140, that captures the patient's gait. The doctor-specified actuation instruction may be communicated from the remote therapy system 140 to the symptom intervention system 110 over the network 160.

Figure 5:
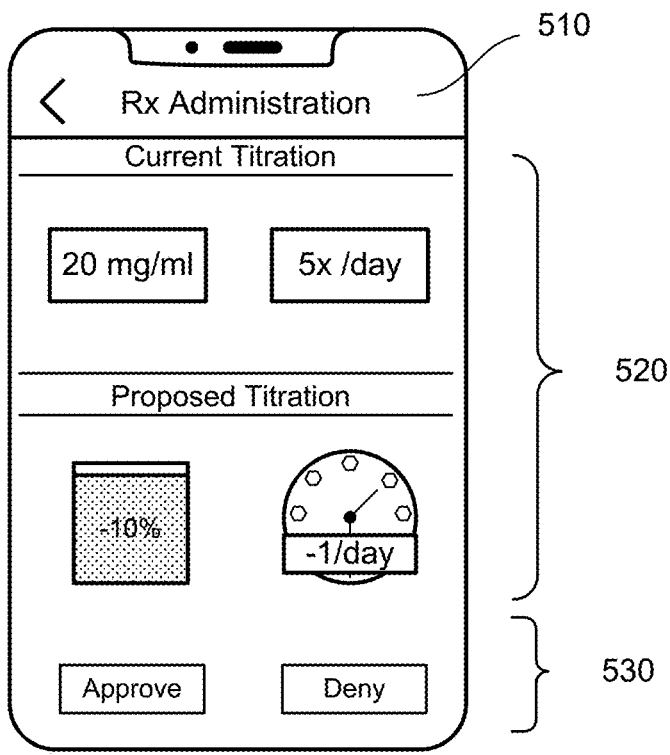
FIG. 5 depicts a GUI for managing chemical stimulus administration modifications determined by a symptom intervention assembly, in accordance with at least one embodiment.
Figure 6:
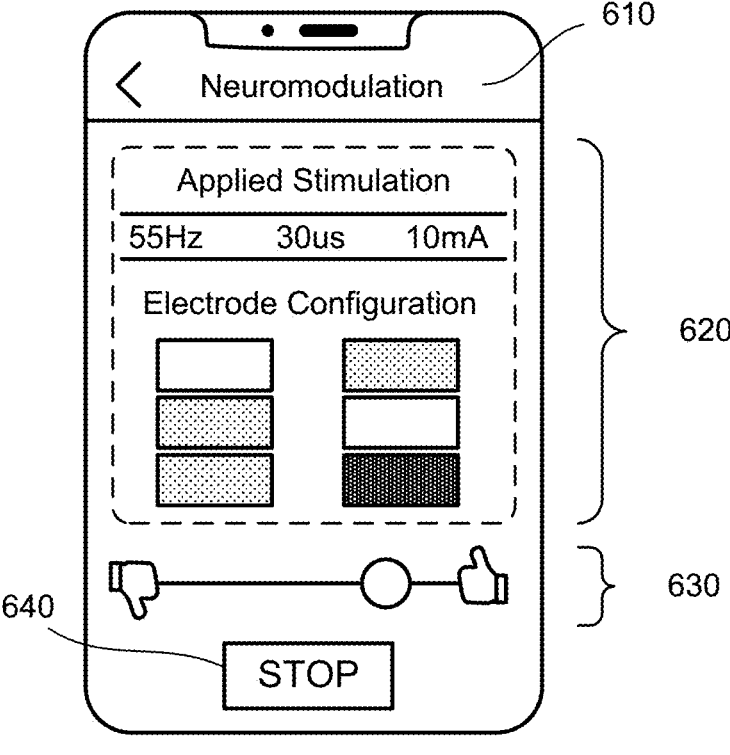
FIG. 6 depicts a GUI for managing neuromodulation applied by a symptom intervention assembly, in accordance with at least one embodiment.

The user device 150 may be a personal computer (PC), a tablet PC, a smartphone, or any suitable device capable of executing instructions that specify actions to be taken by that device. The user device 150 may include a processor (e.g., a central processing unit (CPU), a graphics processing unit (GPU), a digital signal processor (DSP), one or more application specific integrated circuits (ASICs), one or more radio-frequency integrated circuits (RFICs), or any combination of these), a memory, a user interface to receive user inputs or provide outputs to the user (e.g., a visual display interface including a touch enabled screen, a keyboard, microphone, speakers, etc.). The visual interface may include a software driver that enables displaying user interfaces on a screen (or display). The user device 150 may enable a user to manage the symptom intervention assembly 110. For example, the symptom intervention assembly 110 may cause a GUI to be generated at a screen of the user device 150, where the GUI includes input fields to approve, deny, or modify an actuation instruction to be applied to intervene with a symptom. The assembly 110 may also cause a GUI to be generated at the user device 150 that allows the user to provide feedback indicating a measure of approval with the actuation instruction applied. The assembly 110 may cause the GUI to be generated by hosting documents (e.g., HyperText Markup Language (HTML) documents) and transmitting them to a web browser or application of the user device 150 that generates GUI elements at the device 150. Examples of GUIs are shown in FIGS. 5 and 6.

The network 160 may serve to communicatively couple the symptom intervention assembly 110, the remote symptom intervention system 120, the database 130, the remote therapy system 140, and the user device 150. For example, the symptom intervention assembly 110 and the remote therapy system 140 are configured to communicate via the network 160. In some embodiments, the network 160 includes any combination of local area and/or wide area networks, using wired and/or wireless communication systems. The network 160 may use standard communications technologies and/or protocols. For example, the network 160 includes communication links using technologies such as Ethernet, 802.11, worldwide interoperability for microwave access (WiMAX), 3G, 4G, 5G, code division multiple access (CDMA), digital subscriber line (DSL), etc. Examples of networking protocols used for communicating via the network 160 include multiprotocol label switching (MPLS), transmission control protocol/Internet protocol (TCP/IP), hypertext transport protocol (HTTP), simple mail transfer protocol (SMTP), and file transfer protocol (FTP). Data exchanged over the network may be represented using any suitable format, such as hypertext markup language (HTML) or extensible markup language (XML). In some embodiments, all or some of the communication links of the network 160 may be encrypted using any suitable technique or techniques.

Although the components of the system environment 100 are shown as connected over the network 160, one or more components may function without being connected to the network 160. For example, the symptom intervention assembly 110 may function offline when it is not able to connect to the network 160. When the assembly 110 is able to reconnect to the network 160, the assembly 110 may upload monitored activity data, symptom identification results, or determined symptom intervention to the database 130 or the remote therapy system 140 via the network 160.

Symptom Intervention Assembly

FIG. 2 is a block diagram of the symptom intervention assembly 110 of FIG. 1, in accordance with at least one embodiment. The symptom intervention assembly 110 monitors activity data of a user to identify an onset of a symptom and an intervention for the symptom. Components of the symptom intervention assembly 110 include sensors 201, dosing 202, a power source 203, communications circuitry 204, and a microcontroller (MCU) 205. The sensors 201 of the symptom intervention assembly 110 monitor a user's activity data. The symptom intervention assembly 110 includes the MCU 205, which can store and execute a symptom intervention system 220 to identify the onset of a symptom and determine an intervention for the symptom. The symptom intervention assembly 110 can apply the determined intervention through dosing 202.

The sensors 201 measure the user's activity. A user's activity may include movement or body measurements related to movement such as heart rate or respiration rate affected by movement. A user's movement may include movements affected by chemical stimulus, the efficacy of which can be measured through hormone level or biomolecule levels affected by the chemically stimulated hormones. The user's activity can be measured before, during, or after application of an actuation to intervene with the symptom. User activity measured before actuation may be used to determine which actuation instruction to enable. User activity measured during or after the application of the actuation may be used to score the applied actuation. The sensors 201 may be one or more of an IMU, EMG sensor, camera, heart rate sensor, pressure sensor bed or foot pressure sensor, force sensor, glucose monitor, or any suitable sensor for measuring movement or body measurements related to movement. The sensors 201 may include an EMG sensor, which may include electrodes for collecting EMG data, or the symptom intervention assembly 110 may obtain EMG data from electrodes of the dosing 202. The sensors 201 may include a galvanic skin sensor, which may include dedicated electrodes for measuring changes in sweat gland activity on the skin or may use the electrodes of the dosing 202 to collect the galvanic skin response data.

The sensors 201 may be located at various locations on the user's body. For example, a pressure sensor bed may be placed in the user's right shoe to measure the user's right foot pressure as the user completes a gait. A set of sensing electrodes may be placed at the shank of the user's right leg to measure the intended movement data before and during the gait. The sensors 201 may be communicatively coupled to the MCU 205 to provide the measured data for determining or optimizing actuation instructions applied by the symptom intervention assembly 110. In some embodiments, the locations of the sensors 201 includes the joints of the body (e.g., ellipsoid joint and saddle joint). For example, the sensors 201 may measure movement at the ellipsoid and saddle joints using IMU's to determine the quality of a user's grip (e.g., how far the user is able to close their hand into a fist).

The sensors 201 may include a sensor that is not co-located with other sensors of the sensors 201 (e.g., the sensor does not rely upon the power source 203 for power). For example, the sensors 201 may include a camera directed at the user and configured to capture image data of the user's movements. The camera may be communicatively coupled to the symptom intervention system 220 to provide captured image data. The symptom intervention system 220 may then determine an actuation instruction to assist in the user's movement depicted in the image data or user's movement expected to follow the movement depicted in the image data.

The dosing 202 perform actuation instructions determined by the symptom intervention system 220 for intervening with a symptom of a physical condition. The dosing 202 may perform actuation instructions for various types of actuation such as titration (e.g., of a chemical stimulus), neuromodulation, biofeedback, and FES. The dosing 202 may be located at various locations on the user's body. For example, electrodes for neuromodulation may be located at the user's brain and electrodes for FES are located at the user's limbs. The dosing 202 may be communicatively coupled (e.g., wireless or wired) to the symptom intervention system 220 to receive actuation instructions. For example, neuromodulation electrodes may be wired to a controller implanted within the user, which is wirelessly coupled to an MCU of a wearable stimulation array wrapped around one of the user's leg to assist with their walking. In this example, the MCU of the array may include the symptom intervention system 220 and coordinate actuation instructions for both the FES electrodes and the neuromodulation electrodes to improve the user's gait.

The dosing 202 may be actuators that include hardware to perform the various types of actuation. To perform titration, the dosing 202 can include a pump coupled to a tube to deliver doses of a chemical stimulus automatically to the user. To apply neuromodulation, the dosing 202 may include electrodes connected to the user's brain to deliver low voltage electrical stimulation. To apply biofeedback, the dosing 202 may include a speaker, vibrating mechanism, display, LEDs, or a combination thereof. To perform FES, the dosing 202 include an array of electrodes, which may be configurable by the symptom intervention system 220, to apply an electrical signal to stimulate a muscle group and assist with a particular movement (e.g., a gait). In some embodiments, the symptom intervention assembly 110 may leverage actuators from another device (e.g., vibrating mechanisms of the user device 150) by transmitting instructions to the other device to apply an actuation instruction (e.g., biofeedback vibrations).

The power source 203 may be a mobile power source such as a battery or a fixed power source such as an outlet connection to power. The power source 203 may provide power for actuation by the dosing 202. For example, the dosing control module 225 may activate or deactivate an electrical connection between the power source 203 and FES electrodes of the dosing 202 to control electrical stimulation. The power source 203 may provide power for biofeedback actuation that includes mechanical stimulation via a vibrating motor or audio signals output via a speaker to provide cues for the user to walk. In some embodiments, the power source 203 provides power for chemical stimulus administration modification. For example, the power source 203 may support a titration system that involves an external, portable pump that delivers levodopa for Parkinson's disease through a tube (e.g., percutaneous endoscopic gastrostomy with jejunal tube) to the intestine.

The communications circuitry 204 enables the symptom intervention assembly 110 to communicate over a network (e.g., the network 160). The communications circuitry 204 may be configured to establish a connection between the symptom intervention assembly 110 and the Internet using one or more of a Wi-Fi, cellular, local area network (LAN) interface, or any suitable interface for wireless communication. The communications circuitry 204 may be configured to transmit and receive data from communications circuitry of other devices (e.g., other wearable stimulation arrays or a user device). In some embodiments, the communications circuitry 204 may also enable wired communication through various mediums such as fiber-optic, USB, serial, coaxial, or any suitable cable for wired networking.

The MCU 205 represents one or more processors such as a microprocessor, a central processing unit, or the like. More particularly, the processing device may be complex instruction set computing (CISC) microprocessor, reduced instruction set computing (RISC) microprocessor, very long instruction word (VLIW) microprocessor, or a processor implementing other instruction sets, or processors implementing a combination of instruction sets. The MCU 205 may also be one or more special-purpose processing devices such as an application specific integrated circuit (ASIC), a field programmable gate array (FPGA), a digital signal processor (DSP), network processor, or the like. The MCU 205 may be configured to execute instructions for performing the operations and steps described herein.

The MCU 205 hosts and executes a symptom intervention system 220, which includes software modules such as a symptom identifier module 224, a dosing control module 225, a graphical user interface (GUI) module 226, and a model training engine 227. The symptom intervention system 220 includes models, such as a general symptom identification model 228 and a user-specific symptom identification model 229, for identifying the onset of a symptom of a physical condition. The system 220 may also include dosing model 230 for determining an actuation instruction to apply based on the identified symptom. The symptom intervention system 220 includes databases such as an actuation instruction database 221, a user profile database 222, and a physical condition profile database 223. The symptom intervention system 220 may have alternative configurations than shown in FIG. 2, including different, fewer, or additional components. For example, one or more of the databases 221, 222, or 223 may be stored remotely rather than on a memory of the MCU 205 (e.g., contents stored in the database 130) and may be accessible through the network 160. In another example, an additional report generation module may generate a report of the applied actuation and the monitored activity data associated with the actuation and provide the report to the remote therapy system 140.

The software modules of the symptom intervention system 220 may be modified using a scripting engine that enables real-time programmability of the systems. The scripting engine enables new or personalized algorithms to be deployed without a need to update the systems' firmware or reflash the hardware with new code.

The actuation instruction database 221 stores actuation instructions for enabling the dosing 202 to intervene in the occurrence of a symptom of a physical condition of the user. An actuation instruction may specify an actuation type, duration of actuation, location of actuation, any suitable parameter of the actuation, or combination thereof. For example, an actuation instruction for an electrical stimulation signal may include parameters specifying an amplitude (e.g., volts), frequency, and pulse width of the signal, a duration to apply the stimulation to the user, and a location at the user's shank of their left leg to apply the stimulation. An actuation types classifies the actuation into a manner of actuation such as electric, mechanic, haptic, audio, visual, pneumatic, hydraulic, or a combination thereof. Additional examples of actuation types include chemical stimulus administration (e.g., titration), neuromodulation, biofeedback, and FES electrodes. Each actuation type is described in more detail with respect to the description of the dosing 202. The duration of the actuation may vary based on the actuation type. For example, neuromodulation may last shorter (e.g., ten seconds) than biofeedback (e.g., as long as the user is walking). The location of actuation may indicate which hardware components of the symptom intervention assembly 110 apply the actuation. For example, the location of actuation may be a subset of the FES electrodes or a subset of the neuromodulation electrodes of the dosing 202. In another example, the location of actuation may be a particular wearable stimulation array of multiple stimulation arrays worn by the user. Examples of wearable stimulation arrays may be found in U.S. patent application Ser. Nos. 17/397,669 and 17/397,674, filed Aug. 9, 2021, which are incorporated herein by reference.

The user profile database 222 stores information regarding one or more users. The users may be users of the symptom intervention assembly 110, which includes memory to store the user profile database 222. In some embodiments, information of users of the wearable stimulation arrays transmitted to the user profile database 222, which is located at a remote server such as the remote symptom intervention system 120. The user profile database 222 may include user information such as body measurements, movement measurements, and chemical stimulus administration information. Examples of body measurements include height, weight, body mass index, body temperature, heart rate, galvanic skin response, hormone activity, or any suitable measurement of a natural activity the user's body undergoes. Examples of movement measures may include a walking pace, a number of steps taken, an elevation gain, exercises performed, or any suitable measurement of physical movement that the user takes. In some embodiments, chemical stimulus administration is a medical prescription, and the administration information includes when the user takes a medicine, how much medicine the user takes per dose, the type of medicine, or any suitable characteristic of the prescription.

User information stored in the user profile database 222 may be provided by the user manually (e.g., the user entering their height), tracked by a wearable device such as the stimulation array described herein or a wearable fitness tracker (e.g., a smartwatch), or provided by a third party (e.g., a doctor at the remote therapy system 140). The information stored within the database 222 may be edited. For example, a medical doctor at the remote therapy system 140 may update the chemical stimulus administration of the user, and the updates may be transmitted from the remote therapy system 140 to the symptom intervention assembly 110 through the network 160. In another example, the symptom intervention system 220 can store and edit information at the user profile database 222. For example, modifications to the chemical stimulus administration determined by the dosing control module 225 may be stored within the user profile database 222.

The user information stored in the user profile database 222 may also include information tracked by sensors (e.g., the sensors 201 of the symptom intervention assembly 110). For example, the user profile database 222 may store a record of the movement data representing stimulated movement of the user by the dosing 202 of the symptom intervention assembly 110. In some embodiments, the user profile database 222 stores feedback from the user indicating a measure of approval of the symptom intervention. The feedback may be inferred through measurements taken by the symptom intervention assembly 110 or manually provided by the user. For example, the symptom intervention assembly 110 measures and compares user movement assisted by FES with movement assisted by biofeedback, where the FES and biofeedback are intended to help the user with their gait. The symptom intervention assembly 110, which may include a sensor located at the user's shoe, measures kinetic movement data representing movement in a gait (e.g., dorsiflexions) of differing qualities assisted by the two actuation instructions. The symptom intervention assembly 110 compares the kinetic movement data of the movements to kinetic movement data of a neurotypical dorsiflexion and determines that the FES actuation instruction stimulated movement that is more similar to neurotypical movement than the biofeedback instruction stimulated. The result of this comparison may be stored in the user profile database 222 as feedback indicating that FES stimulation works better for the user than biofeedback for improving dorsiflexion.

In another example, a user manually provides feedback that is stored in the user profile database 222. The symptom intervention assembly 110 may be communicatively coupled to a user device (e.g., the user device 150) through which the user can provide feedback of the intervention applied, or proposed to be applied, by the symptom intervention assembly 110. The feedback may indicate a measure of comfort, effectiveness, or approval of the intervention. Example GUIs through which a user can provide feedback are shown in FIGS. 5-6.

The physical condition profile database 223 stores information regarding one or more physical conditions and corresponding symptoms. Example physical conditions include Parkinson's disease, multiple sclerosis, cerebral palsy, having suffered from a stroke, or any other condition that affects a user's ability to move as desired. Each physical condition may be associated with respective symptoms that indicate that the user is affected by the physical condition. Parkinson's disease may be associated with impairments to movement such as tremors, rigidity (e.g., gait freeze or freeze of gait (FOG)), bradykinesia, and imbalance. Multiple sclerosis may be associated with similar impairments to movement such as tremors and imbalance and additional impairments such as ataxia (i.e., unstable walking) and clumsiness of a limb. Cerebral palsy may be associated with similar impairments to movement such as tremors, rigidity, and difficulty walking (e.g., crouch gait).

The physical condition profile database 223 may store symptom signal profiles for symptoms of a physical condition. Symptom signal profiles may be a quantitative representation of the symptom as it is experienced by a given user. For example, a symptom signal profile of a tremor may include kinematic signals measured by IMU sensors located near the muscle group experiencing the tremor (e.g., at the user's hand or forearm). In another example, a symptom signal profile of imbalance may include kinematic signals measured by IMU sensors at a left leg and a right leg, the signals demonstrating muscles at one leg being weaker than muscles at the other. Symptom signal profiles may be collected across a population of users having a physical condition, and signals of the profiles may be averaged to obtain a general symptom signal profile. The symptom signal profiles may characterize respective symptoms throughout their duration (e.g., from an onset of a tremor to when the tremor stops). The onset of a symptom may be characterized by an initial portion of a symptom signal profile. For example, for a symptom signal profile including kinematic signals of a FOG over time, the onset of the FOG may be characterized by the first second of the symptom signal profile.

The physical condition profile database 223 may store information related to the onset of a symptom in addition or alternative to the symptom signal profile. An onset of a symptom may be characterized by contextual information such as a schedule or a location of the user. For example, a FOG may occur when the user is walking in a large crowd or entering an elevator, activities which can be deduced by a location or a schedule of the user. The onset of a symptom may be characterized by activity information such as a heart rate, respiration rate, hormone activity, or information about an administration of a chemical stimulus. For example, FOG may occur when a user is distressed, anxious, or frightened, which may coincide with an increased heart rate or respiration rate. In another example, FOG may occur when a chemical stimulus's efficacy has diminished since the time of its dose. A level of insulin of a user, an example of hormone activity, when experiencing FOG and information about when a chemical stimulus for reducing FOG occurrences was administered may be used to characterize the onset of the symptom. The database 223 may store contextual information and activity information associated with the onset or full duration of the symptom.

The symptom identifier module 224 identifies an onset of a symptom of a user's physical condition. The onset of a given symptom may be one or more measurable signals or information indicating that the user's monitored movement is transitioning to movement affected by the given symptom. The measurable signals (e.g., movement signals) and information (e.g., contextual information) may be measured at a time period between the end of neurotypical movement, or movement unaffected by the physical condition, and the start of movement impacted by the symptom. The symptom identifier module 224 may monitor a user's activity data, and use the monitored activity data to identify the onset of a symptom. Activity data may be monitored using the sensors 201 or provided manually (e.g., a user or doctor provides the symptom intervention system 220 with the user's medical prescription).

The symptom identifier module 224 determines whether to intervene with an actuation. In some embodiments, the symptom identifier module 224 determines to intervene when the onset of a symptom is identified with a confidence score meeting or exceeding a threshold confidence score. The symptom identifier module 224 determines not to intervene when the onset of a symptom is identified with a confidence score below a threshold confidence score. The symptom identifier module 224 may use one or more threshold confidence scores for respective symptoms. For example, a threshold confidence score of 80% confidence may be used for identifying a tremor for Parkinson's disease while a threshold confidence score of 60% may be used for crouch gait for CP. The symptom identifier module 224 may adjust the threshold confidence score. For example, as the symptom intervention system 220 receives user feedback of the applied actuation indicating that the applied actuation is approved, the symptom identifier module 224 may lower the threshold confidence score.

The symptom identifier module 224 may identify both the onset of a symptom and which symptom of various symptoms whose onset is being identified. The symptom identifier module 224 may apply a model to monitored activity data, where the model outputs a symptom and an associated confidence score that the identification is accurate. By applying the model to activity data monitored at a time period between the end of neurotypical movement and the initial impact of the symptom on the user, the symptom identifier module 224 can identify the onset of the symptom of a physical condition. The model may be a machine learned model trained on data monitored at the onset of a symptom, and thus able to identify subsequent onsets. Training of the models is described further in the description of the model training engine 227.

The symptom intervention system 220 may manage a model for each symptom it identifies, where the respective models are trained on data for the respective symptom. For example, a first machine-learned model is trained with data representing the onset of a tremor for Parkinson's disease and a second machine-learned model is trained with data representing FOG for Parkinson's disease. The symptom identifier module 224 may apply both models to monitored activity data and determine that the user is experiencing FOG with a confidence score of 85%, as determined by the second machine-learned model, and the user is experiencing a tremor with a confidence score of 5%, as determined by the first machine-learned model. Because the confidence score is greater for one symptom than another, the symptom identifier module 224 may identify that the user is experiencing the onset of the symptom with greater confidence score (e.g., identifies FOG and not tremors).

Various types of activity data may be used to identify an onset of a symptom. Examples of which include movement signals, hormone activity, kinematic scores, movement cadence, gait report, posture changes, and fatigue. The symptom identifier module 224 may apply movement signals measured by the sensors 201 to a machine-learned model trained on movement signals to identify an onset of a symptom of a physical condition. In one example, the symptom identifier module 224 receives movement signals measured at an IMU sensor and foot pressure sensor of the sensors 201. These monitored movement signals may represent the kinematics of a toe-off in a gait cycle as captured at a leg and foot at one side of the user's body. The symptom identifier module 224 then applies the received movement signals to a machine-learned model trained on movement signals representative of shuffling gait, a symptom of physical conditions such as Parkinson's disease and having suffered from a stroke. Using the machine-learned model, the symptom identifier module 224 may determine that an actuation instruction should be applied to intervene with the shuffling gait. For example, the module 224 may notify the dosing control module 225 of the onset of the shuffling gait after the machine-learned model identifies its onset in the monitored movement signals with a confidence score above a threshold confidence score.

The symptom identifier module 224 may apply hormone activity measured by the sensors 201 to a machine-learned model trained on hormone activity to identify an onset of a symptom of a physical condition. Hormone activity may include measurements for a level of a hormone or a biomolecule affected by the hormone. In one example, the symptom identifier module 224 receives glucose levels measured at a glucose monitor. These monitored glucose levels may be commensurate with the user's insulin levels and may represent the current efficacy of a chemical stimulus taken to treat physical condition symptoms. For example, levodopa-carbidopa is a chemical stimulus taken to treat symptoms of Parkinson's disease. However, the intake of levodopa-carbidopa may affect insulin-stimulated glucose transport. Therefore, a glucose monitor may show that a user has a certain glucose level when effects of levodopa-carbidopa (e.g., promoting dopamine) are active (e.g., an "on" period) and a different glucose level when the effects of levodopa-carbidopa are diminished (e.g., an "off" period). The symptom identifier module 224 then applies the received glucose levels to a machine-learned model trained on glucose levels representative of users experiencing an "off" period of levodopa-carbidopa.

When levodopa-carbidopa users experience "off" periods, they are more likely to experience symptoms of Parkinson's disease. Accordingly, using the machine-learned model, the symptom identifier module 224 may determine that an "off" period is occurring and that an actuation instruction should be applied to intervene with a symptom of Parkinson's. For example, the module 224 may determine that an onset of a Parkinson's disease symptom is likely occurring or will occur due to the detected "off" period of the chemical stimulus. The module 224 may then trigger the dosing control module 225 to determine a modification to the titration of levodopa-carbidopa (e.g., time between doses or amount administered at a particular dose). In some embodiments, the module 225 may also determine an actuation instruction that includes generating a notification for the user (e.g., at the user device 150) to take their dose of the chemical stimulus (e.g., a pill) so that dose can metabolize and intervene with the symptom in a timely manner. An example of this determination is further described in the description of FIG. 7.

The symptom identifier module 224 may determine kinematic scores from movement signals measured by the sensors 201, and apply the determined kinematic scores to a machine-learned model trained on kinematic scores to identify an onset of a symptom of a physical condition. In one example, the symptom identifier module 224 receives movement signals measured at IMU sensors at the knee joints of the user's left and right legs. Comparison of these monitored movement signals may represent the symmetry of a user's gait. For example, the symptom identifier module 224 may compare kinematic signals representing the swing phase of a user's gait at their left knee joint to the corresponding kinematic signals at the user's right knee joint. In response to determining a high level of symmetry between the two sets of right and left knee joint kinematic signals, the symptom identifier module 224 may determine not to modify the administration of a chemical stimulus taken by the user to treat their physical condition. In response to determining a low level of symmetry between the two sets of kinematic signals, the symptom identifier module 224 may determine to modify the administration of the chemical stimulus. The module 224 may determine whether a symmetry level is high or low using various signal processing techniques such as determining a cross-correlation, time-shifting, and determining a difference between the two signals. The module 224 may apply the determined level of symmetry to a machine-learned model trained on symmetry levels representative of an imbalanced gait, which is a symptom of physical conditions such as Parkinson's disease and MS. Using the machine-learned model, the symptom identifier module 224 may determine that an actuation instruction should be applied to intervene with the imbalanced gait. For example, the module 224 may notify the dosing control module 225 of the onset of the imbalanced gait after the machine-learned model identifies its onset in the low level of symmetry between kinematic signals at the user's two knee joints.

The symptom identifier module 224 may apply a cadence of movement signals measured by the sensors 201 to a machine-learned model trained on movement cadence to identify an onset of a symptom of a physical condition. In one example, the symptom identifier module 224 receives movement signals measured at an IMU sensor located at a user's leg to measure kinematic signals representative of the user's gait. The symptom identifier module 224 determines a frequency response of the user's gait, or the user's gait cadence. As gait movements are typically cyclic in nature, a neurotypical gait does not deviate substantially from an average frequency. However, a user with a physical condition such as Parkinson's disease may experience symptoms such as bradykinesia, which can suddenly slow or freeze the user's gait. The symptom identifier module 224 may determine a change in gait cadence, and determine whether the change warrants triggering the dosing control module 225 to modify an administration of a chemical stimulus. In one example, the module 224 determines that the cadence has decreased greater than a threshold amount and triggers the module 225 to modify a titration of levodopa taken by the user to treat their Parkinson's disease. In another example, the module 224 determines that the cadence has reached zero, indicating that the user may be experiencing FOG, and trigger the module 225 to modify the titration of levodopa. In yet another example, the module 224 applies the change in gait cadence to a machine-learned model trained on gait cadence changes representative of bradykinesia. Using the machine-learned model, the symptom identifier module 224 may determine that an actuation instruction should be applied to intervene with the bradykinesia.

The symptom identifier module 224 may determine gait report using movement signals measured by the sensors 201 and apply the gait report to a machine-learned model trained on gait reports to identify an onset of a symptom of a physical condition. The symptom identifier module 224 uses historical movement signals measured at a muscle group used in a gait cycle (e.g., a foot, shank, a thigh, or combination thereof) to create a baseline gait profile. A single gait cycle may be composed of a stance phase and a swing phase. A stance phase may include, in sequence of the gait cycle, a heel strike, a loading response, mid-stance, terminal stance, and pre-swing. A swing phase may include, in sequence of the gait cycle, a toe-off, mid-swing, and terminal swing. The baseline gait profile may include movement signals representative of one or more of the phases or the movements within the respective phases. For example, a baseline gait profile may include kinematic signals measured through a foot pressure sensor as a user is moving through the stance phase and rested such that the baseline gait profile represents a relatively optimal stance phase performance for the user. The baseline gait profile can be used by the symptom identifier module 224 to compare to subsequently monitored movement signals by the foot pressure sensor to determine how the user is performing their stance phase relative to their baseline performance. This comparison may be referred to herein as a "gait report."

In one example of using a gait report to identify an onset of a symptom of a physical condition, the symptom identifier module 224 receives movement signals measured at an IMU sensor and foot pressure sensor of the sensors 201. These monitored movement signals may represent the kinematics of a swing phase in a gait cycle as captured at a leg and foot at one side of the user's body. The symptom identifier module 224 creates a baseline gait profile of the user's swing phase using historical movement signals measured at the user's leg (e.g., shank muscle) and foot. The symptom identifier module 224 determines a score for a gait report based on a comparison of the monitored movement signals to the baseline gait profile. For example, the symptom identifier module 224 may determine the similarity of the monitored kinematic signals to the historical kinematic signals in the baseline gait profile. The determined level of similarity may be a gait report score within the gait report. The symptom identifier module 224 may apply scores within the gait report to a machine-learned model trained on gait reports representative of shuffling gait, a symptom of physical conditions such as Parkinson's disease and having suffered from a stroke. Using the machine-learned model, the symptom identifier module 224 may determine that an actuation instruction should be applied to intervene with the shuffling gait.

In some embodiments, the symptom identifier module 224 may identify an onset of a symptom of a physical condition using a comparison to movement signals taken when the user is moving without assistance from a chemical stimulus. Similar to the baseline gait report, a baseline symptom profile may be created by the module 224, where the baseline symptom profile is created using historical movement data representative of movement while a user is experiencing the symptom without assistance from a chemical stimulus. The baseline symptom profile can be similar to the baseline gait report in that they both represent the historical movement of a user, but the symptom profile may be generally applicable to movements in addition to a gait. The symptom identifier module 224 may compare monitored movement signals to the baseline symptom profile to determine a movement score representative of a level of similarity the user's current movement is to movement when the user is experiencing the symptom without chemical stimulus assistance. The module 224 may use a threshold score to identify that the user is experiencing an onset of a symptom. For example, the movement score indicates a level of similarity that meets a threshold score indicating that the user is experiencing a tremor. In response, the module 224 may trigger the dosing control module 225 to determine a modification to the chemical stimulus administration. In some embodiments, the symptom identifier module 224 may apply the determined movement score to a machine-learned model trained on movement scores to identify an onset of a symptom of a physical condition. If the machine-learned model outputs a confidence score above a threshold confidence score that a user is experiencing, for example, tremors of their Parkinson's disease, the module 224 may notify the dosing control module 225 of the onset of the tremors.

The symptom identifier module 224 may apply image data captured by the sensors 201 to a machine-learned model trained on image data to identify an onset of a symptom of a physical condition. Cameras may capture a user's posture or change therein, which may indicate the onset of a symptom of a physical condition. In one example, the symptom identifier module 224 receives image data captured at a camera of the sensors 201. The captured image data depicts a user's change in upright posture to an imbalanced posture (e.g., the leg muscles of one leg experience spasticity and causes the imbalance). The symptom identifier module 224 then applies the image data to a machine-learned model trained on image data representative of spasticity, a symptom of Parkinson's disease, CP, and MS. The machine-learned model may identify the onset of spasticity above a threshold confidence score, and the symptom identifier module 224 may trigger the dosing control module 225 to apply an actuation instruction to intervene with the spasticity.

The symptom identifier module 224 may apply data representative of a level of fatigue to a machine-learned model trained on data representative of fatigue to identify an onset of a symptom of a physical condition. Fatigue may be associated with diminishing effects of a chemical stimulus (e.g., an "off" period of levodopa) and correlated with an increased in likelihood that an onset of a physical condition's symptom will occur. The symptom identifier module 224 may apply EMG signals, which can represent a user's level of fatigue, to a machine-learned model to identify an onset of a symptom. EMG signals reflect muscle electroactivity, and their frequency may reflect the level of fatigue. As a user grows fatigued, the frequency of EMG signals may decrease. In one example, the symptom identifier module 224 receives EMG signals measured at an EMG sensor of the sensors 201. The module 224 may apply the received EMG signals to a machine-learned model trained on historical EMG signals measured when the user is rested such that the machine-learned model identifies whether the received EMG signals indicate the user is rested or fatigued. Additionally or alternatively, the symptom identifier module 224 may create a rested frequency response profile of the user using historical EMG signals, where the rested frequency response profile indicates the average frequency response of a user when they are rested (e.g., performing a gait cycle without feeling fatigued). Based on a comparison of the received EMG signals to the rested frequency response profile, the symptom identifier module 224 may identify that an onset of a symptom is likely to occur or is occurring. This comparison or the received EMG signals themselves may be measures of the user's fatigue. The module 224 may also apply a machine-learned model to the results of the comparison to identify the onset of the symptom. In response to determining that the measure of fatigue is indicative of a likely onset of the user's physical condition symptom, the module 224 may notify the dosing control module 225 of the onset of the symptom to determine an appropriate actuation instruction.

The symptom identifier module 224 may determine context information to identify whether an onset of a symptom is occurring. Symptoms of physical conditions may be more likely to occur under certain environmental conditions. For example, those with Parkinson's disease are more likely to experience FOG when they are walking through narrow passages or doorways, entering or exiting elevators, in a busy crowd, or when they are anxious or frightened. The sensors 201 may provide information insightful to the user's environment. For example, a heart rate sensor of the sensors 201 may indicate that the user's heart rate is becoming elevated and is experiencing anxiety. Although not depicted, the symptom intervention assembly 110 may be GPS enabled such that the assembly 110 can determine a location of the user. Alternatively, the assembly 110 can periodically request the user's location from a GPS-enabled device that it is communicatively coupled with through the communications circuitry 204. In one example, a GPS location of the user may indicate that the user is at a sports venue and is more likely to be within a busy crowd or walk through narrow passageways (e.g., bleachers). IN some embodiments, context information is provided by the user and accessed by the symptom identifier module 224. For example, the user provides their schedule of events to a calendar application on their device (e.g., the user device 150) and the symptom identifier 224 queries the calendar application to determine the event that the user is likely to be doing at the current time. The symptom identifier module 224 may quantify this context information and apply a machine-learned model trained on context information to identify that the user is experiencing a symptom (e.g., FOG).

The various types of activity data for identifying an onset of a symptom by the symptom identifier module 224 are described herein individually but any suitable combination of these data types may be used to identify the onset of the symptom. One or more of the movement data, hormone activity, kinematic scores, cadence of movement signals, gait report, movement score from a comparison using a baseline symptom profile, image data representative of a user's change in posture, data representative of a measure of fatigue, or context information may be a dimension of a feature vector. For example, the symptom identifier module 224 generates a feature vector that combines movement data, hormone activity, and context information as features in the vector for input into a machine-learned model that is trained on feature vectors of the three corresponding activity data types measured when the user is experiencing a symptom of a physical condition. The symptom identifier module 224 may apply weights to generating the feature vector. For example, if the GPS-enabled device has been providing erroneous GPS traces, the GPS location used in the context information may be inaccurate and thus, receive a smaller weight than activity data types that have been more reliable such as, for example, movement data measured by IMU's worn by the user. The symptom identifier module 224 may adjust the weights based on user feedback of the corresponding applied actuation instruction.

The dosing control module 225 determines actuation instructions to apply through the dosing 202. The dosing control module 225 may be triggered by the symptom identifier module 224 such that it determines which actuation instruction to apply in response to an identified onset of a symptom by the module 224. The dosing control module 225 may determine one or more actuation instructions to apply, where each instruction has a corresponding type. For example, the module 225 may determine to apply a biofeedback actuation instruction and determine an actuation instruction for adjusting a chemical stimulus administration (e.g., titration of levodopa). The dosing control module 225 may determine which actuation instruction of the instructions within the actuation instruction database 221 to apply depending on the identified onset of the symptom (e.g., the symptom and characteristics thereof).

Prior to determining a modification to the administration of a chemical stimulus, the dosing control module 225 may identify the chemical stimulus administered to a user to treat a physical condition of a user. The administration of the chemical stimulus, which may be a medical prescription, may be characterized by an amount of a medication or a time at which the medication is to be taken. The module 225 may identify the chemical stimulus by querying the user profile database 222 for a list of chemical stimulus taken by the user. In some embodiments, the symptom identifier module 224 may identify which physical condition's symptom, the onset of which is or is about to occur, and provide the identified symptom and physical condition to the dosing control module 225. The user profile database 222 may be queried by the symptom or physical condition to identify which chemical stimulus is being taken to treat the condition. In some embodiments, the dosing control module 225 identifies the chemical stimulus based on a user's specification of a particular physical condition for which they are using the symptom intervention assembly 110, and the module 225 is identifies the stimulus based on the user's specification.

The dosing control module 225 can determine a modification to the administration of a chemical stimulus. Modifications can include increasing or decreasing the amount of a chemical stimulus administered (e.g., titrated) or changing the time at which the chemical stimulus is administered. In some embodiments, the dosing control module 225 may determine the modification based on an "on" or "off" period of the chemical stimulus. A patient using a chemical stimulus to treat their physical condition may experience "on" periods when the stimulus is effective and "off" periods when the stimulus is not working as well and symptoms of the physical condition begin to remerge. For example, the module 225 determines an "on" time duration of the administration of the chemical stimulus, where the "on" time duration begins at a time when the chemical stimulus is administered and ends at an onset of a symptom after that time. This onset may be identified by the symptom identifier module 224. The module 225 can determine an "off" time duration of the administration of the chemical stimulus, where the "off" time duration begins at an onset of the symptom (e.g., the onset at the end of an "on" period) and ends at a time that the chemical stimulus is administered again.

The dosing control module 225 may compare the "on" and "off" durations to determine how to modify the administration of the chemical stimulus. For example, in response to determining that the "off" time duration is greater than the "on" time duration, the module 225 may determine to modify the timing of a dose of levodopa to be earlier than previously scheduled. To determine an amount by which the dosage or timing of the chemical stimulus's administered should be changed, the dosing control module 225 may use a model associating differences in "on" and "off" periods to historical modifications of chemical stimulus by medical professional. The model may be a machine-learned or statistical model that determines or interpolates a likely modification based on an input difference between "on" and "off" periods. In some embodiments, the dosing control module 225 may compare "on" or "off" periods to expected "on" or "off" periods and determine that a presently measured period deviates from the expected period over a threshold amount.

In some embodiments, the dosing control module 225 provides a notification that the administration of the chemical stimulus should be modified, and may recommend a modification within the notification. For example, the dosing control module 225 may generate a notification indicating that the dosage amount of levodopa is recommended to be decreased by 10% and transmit it to the remote therapy system 140 over the network 160 using the communications circuitry 204. In addition to determining a modification of a chemical stimulus, the dosing control module 225 may use the determined "on" and "off" periods for a chemical stimulus to determine other actuation instructions such as applying neuromodulation, biofeedback, FES, or a combination thereof. The dosing control module 225 may use the dosing model 230 to determine the recommended modification.

The dosing control module 225 can use characteristics of a symptom to determine how to modify an administration of a chemical stimulus. The characteristics may include a severity of amplitude or frequency of monitored activity data. In some embodiments, the dosing control module 225 can compare movement signals measured by the sensors 201 to signals of a symptom profile, which is further described with reference to the symptom identifier module 224, and use the comparison to determine the modification to the administration. For example, the currently monitored movement signals can show that a user is experiencing tremors that have an amplitude or frequency that deviates from those reflected in their symptom profile for their tremors, and the dosing control module 225 may determine an amount by which the current tremors deviates from the profile's. This deviation may represent the severity of the tremors. In response to determining that the severity of the tremors as worsened (e.g., increased amplitude or frequency), the dosing control module 225 may determine to increase the dosage or shorten the time between two consecutive doses of the chemical stimulus. In response to determining that the severity of the tremors as improved (e.g., decreased amplitude or frequency), the dosing control module 225 may determine to decrease the dosage or increase the time between two consecutive doses of the chemical stimulus.

The dosing control module 225 may also determine various actuation instructions in addition to chemical stimulus dosing instructions, such as neuromodulation instructions. The dosing control module 225 may determine actuation instructions for applying neuromodulation. The dosing control module 225 may determine stimulation parameters of the neuromodulation such as a frequency, pulse width, or amplitude of the stimulation signals. The electrodes placed at the user's brain may be configurable such that the dosing control module 225 can determine which electrodes should serve as a cathode, anode, or be disconnected (i.e., not receiving or transmitting electrical stimulation at the brain). The dosing control module 225 may determine to depolarize neurons of a user's brain by determining which of the configurable neuromodulation electrodes should operate as a cathode. To hyperpolarize neurons of the user's brain, the dosing control module 225 may determine which of the configurable neuromodulation electrodes should operate as an anode.

The dosing control module 225 may use characteristics of a symptom to determine neuromodulation parameters to apply. Characteristics of the identified symptom onset may include an acceleration or speed at which the user's limb shake during a tremor, a deceleration of leg movement over time related to slowing gait, an increase in knee joint angle related to crouch gait, or any suitable quantifiable parameter of a symptom. The dosing control module 225 may use characteristics of a symptom and a history of previous neuromodulation parameters to identify a neuromodulation operation to mitigate the identified symptom or symptom onset. For example, the module 225 may determine an amplitude of IMU signals tracking the acceleration of a user's tremors at a hand. The module 225 may determine the amplitude is similar to a previously detected amplitude that is associated with a historical neuromodulation operation having a particular stimulation signal (e.g., frequency, pulse width, amplitude) and electrode configuration (e.g., which electrodes function as anodes, cathodes, or are disconnected). The historical neuromodulation operations or feedback thereof may be characteristics of the user.

The dosing control module 225 may apply the dosing model 230 to characteristics of an identified symptom onset to determine a neuromodulation operation. In some embodiments, the dosing control module 225 may estimate parameters of a neuromodulation operation (e.g., interpolate an amplitude or frequency of previously applied electrical signals) to apply and intervene with the identified symptom. In some embodiments, the module 225 may also determine whether the user provided positive feedback or previously monitored movement of assisted movement with the historical neuromodulation indicated effective symptom intervention.

The dosing control module 225 may apply the neuromodulation operation through a wearable neuromodulation system that includes electrodes coupled to the user, where the wearable neuromodulation system can include an implanted device with electrodes contacting the user's brain and a controller wired to the electrodes. In some embodiments, the wearable neuromodulation system is a device external to the user with electrode contacts contacting the user's skin and configured to apply neuromodulation to neurons without penetrating the skin (e.g., contacts neurons at the user's leg).

In some embodiments, the dosing control module 225 uses a change in a frequency at which the onset of a symptom is identified to determine the actuation instruction to apply. The change in symptom frequency may be determined using the onsets identified by the symptom identifier module 224. Based on the changes in symptom frequency, the module 225 can determine electrical stimulation parameters for neuromodulation or a configuration of electrodes providing the neuromodulation. For example, the dosing control module 225 can determine to decrease the frequency of electrical stimulation signal applied to the user's neurons (e.g., when a decrease in the frequency is associated with a decrease in the occurrence of the symptom). In another example, the dosing control module 225 can determine a particular combination of neuromodulation electrodes that should serve as cathodes, anodes, or be disconnected, where the particular combination is determined to be used responsive to a particular change in symptom frequency (e.g., when the frequency increases).

The dosing control module 225 may determine actuation instructions for applying biofeedback. The dosing control module may determine a type of biofeedback to apply (e.g., audio, visual, or haptic). The dosing control module may determine where to apply the biofeedback. For example, the user may be using two or more wearable devices that include vibrating mechanisms of the dosing 202 through which the symptom intervention assembly 110 can apply haptic biofeedback. The dosing control module 225 may determine which of the wearable devices to activate vibrations from (e.g., at the leg to help with a user's legs or at the arm to help promote balanced arm swings while walking). In this way, the dosing control module 225 can provide biofeedback to the user that includes sensory cues to promote a neurotypical movement in the user responsive to determining that the user is experiencing a symptom of their physical condition.

The dosing control module 225 may determine one or more actuation instructions to apply based on conditions for applying the one or more of the actuation instructions. The conditions may be based on the activity data used to identify the onset of the symptom. The conditions may include the type of movement that the user is performing, the user's location, heart rate, intended movement (e.g., based on measured EMG signals), time of day, or user's schedule of events. In some embodiments, the actuation instruction database 221 also stores rules or conditions for the dosing control module 225 to determine which actuation instructions to apply. For example, the dosing control module 225 may determine that the user is at a concert, according to information provided on a calendar application on the user device 150, and determine that biofeedback of audio guidance for walking is inappropriate to apply due to the volume of the event drowning out the volume of the audio guidance. Instead, the module 225 may determine to apply neuromodulation or FES. The conditions may be optimized based on user feedback. For example, in response to the user providing a measure of low approval with biofeedback being provided at a certain time of day or location, the dosing control module 225 may reduce the frequency at which biofeedback is provided at that time or location.

The GUI module 226 generates for display GUIs through which a user can manage the functions of the symptom intervention assembly 110. For example, a user can provide feedback of applied actuation instructions or control the actuation instructions performed by the symptom intervention assembly 110 to intervene with a symptom. A GUI may be generated on a user device coupled to the symptom intervention assembly 110. The GUI module 226 may display information describing the intervention such as properties of an applied neuromodulation signal and through which electrodes the signal is applied (e.g., the identification numbers of the electrodes serving as the anodes and cathodes). The GUI module 226 may provide an interactive user interface that includes various buttons, toggles, menus, etc. through which a user can manage the intervention determined or applied by the symptom intervention assembly 110. FIGS. 5-6 show example GUIs that may be generated by the GUI module 226.

The model training engine 227 trains a model to identify an onset of a symptom of a physical condition based on activity data. The model training engine 227 may train a machine learning model in multiple stages. In a first stage, the model training engine 227 may use activity data (e.g., movement signals, hormone activity, chemical stimulus administration data) collected across one or more users (e.g., a population of Parkinson's disease patients) to train a machine learning model. This data from a population of users may be referred to as "general data" or "generalized data." The model training engine 227 may label the general data with a label representative of whether the generalized data coincided with the occurrence of an onset of a symptom of a physical condition. The model training engine 227 creates a first training set based on the labeled general data. The model training engine 227 trains a machine learning model (e.g., the general symptom identification model 228), using the first training set, to identify the onset of a symptom. In some embodiments, the machine learning model is configured to receive, as an input, activity data (e.g., from the sensors 201) or a feature vector of activity data (e.g., determined by the symptom identifier module 224), and output a confidence score associated with the identification of the onset of the symptom.

In a second stage of training, the model training engine 227 can use user-specific activity data (e.g., collected by the sensors 201). The model training engine 227 creates a second training set based on previously identified symptom onsets (e.g., by the trained general symptom identification model 228) and the data representative of measured movement collected from the user of the symptom intervention assembly 110 (i.e., user-specific data). The identified symptom onsets, depending on the success of the corresponding applied actuation (e.g., as indicated by user feedback), may serve as labels for the user-specific data. If a previously determined actuation instruction resulted in symptom intervention that was effective or comfortable, the model training engine 227 may create the second training set that includes user-specific data labeled to indicate the symptom was correctly identified in the activity data. The model training engine 227 then re-trains the machine learning model using the second training set such that the machine learning model is customized to the user's activity. For example, the model training engine 227 may re-train the general symptom identification model 228 such that the re-trained model is the user-specific symptom identification model 229. The dosing model 230 may also be trained by the model training engine 227 similarly in stages. A first stage may use dosing data from a general population of users and the second stage may use user feedback to create a second training set for retraining the dosing model 230.

To create a training set, the model training engine 227 may determine one or more feature vectors associated with measured activity data (e.g., a feature vector representing a combination of movement signals, hormone activity, and chemical stimulus administration). For example, the model training engine 227 may determine a feature vector characterizing movement signals and hormone activity associated with an onset of a tremor of Parkinson's disease.

In some embodiments, the model training engine 227 may retrain a machine-learned model using feedback of a modification to a chemical stimulus administration determined by the dosing control module 225. The model training engine 227 receives feedback of the determined modification indicating a measure of approval that the user has with the determined modification. For example, the user may provide feedback through a GUI, where the feedback is an approval or rejection of the determined modification. The model training engine 227 may modify an association between the identified onset of the symptom of the physical condition and the monitored movement signals that were used to identify the onset. For example, in response to the user providing a measure of approval indicating disapproval, the model training engine 227 reduces a weight applied to signals from the same source as the monitored movement signal. If the monitored movement signals were collected from a foot pressure sensor, the model training engine 227 may reduce a weight of pressure signals from the foot pressure sensor, where the weight is used to generate a feature vector, which itself can be used to train a machine-learned model. When the modified association including the reduced weight is used to retrain a machine-learned model, the model training engine 227 may cause the likelihood of subsequent similar symptom identifications based on foot pressure sensor data to decrease.

In response to the user providing a measure of approval indicating approval of the modification to the chemical stimulus administration, the engine 227 may increase a weight applied to signals from the same source as the monitored movement signal. In addition or alternative to an association between the identified symptom onset and the monitored movement signals being adjusted, an association between the identified symptom and the determined actuation (e.g., the modification to the chemical stimulus administration) may also be modified. Examples of measures of approval may include direct feedback such as a rating of the applied actuation or indirect feedback such as a request to modify the actuation (e.g., a request to stop the actuation), which may indicate disapproval with the applied actuation.

The general symptom identification model 228 is configured to identify an onset of a symptom of a physical condition. There may be general models for respective symptoms or physical conditions, depending on the training data used to train the general models. For example, general models can be maintained for each of a tremor, FOG, and bradykinesia of Parkinson's disease. The general symptom identification model 228 receives, as input, data representing the activity measured by the symptom intervention assembly 110 and outputs an identification of or confidence score associated with an identification of an onset of a symptom of a physical condition. The general symptom identification model 228 may receive activity data collected across a population of users of the symptom intervention assembly 110 experiencing a particular symptom of a physical condition.

The user-specific symptom identification model 229 can be trained by the model training engine 227 using activity data collected from the sensors 201 such that data for training is specific to the user of the symptom intervention assembly 110. The model 229 may be obtained by re-training the general symptom identification model 228. Because the model 229 is trained on user-specific activity data, the model 229 enables the symptom intervention assembly 110 to be personalized to the user and improve its accuracy in identifying onsets of symptoms as experienced by the user, which in turn improves the determined actuation (e.g., the modification of a chemical stimulus administration). The user-specific symptom identification model 229 may, similar to the general symptom identification model 228, be configured to identify, for various symptoms or physical conditions, a corresponding onset.

In some embodiments, the symptom intervention system 220 includes a machine-learned model (e.g., the dosing model 230) for determining a modification to a chemical stimulus administration. The model training engine 227 may create training data based on historical modifications to stimulus administrations, which may include prescription or titration changes that medical professionals have made, an anonymized profile of a patient's symptom history and physical characteristics, or any suitable information correlating a modification to a change in symptoms experienced over time. The model training engine 227 may train the dosing model 230 using the training data to output a recommended modification to a chemical stimulus administration based on a user's symptom progress over time. The symptom identifier module 224 may track the user's symptom progress and store relevant data in the user profile database 222.

The relevant data indicative of the user's symptom progress may include a change in frequency of identifying the symptom, a change in severity of the symptom (e.g., the amplitude of the movement signals of a user's tremors are increasing), the appearance of a symptom previously not affecting the user, the disappearance of a symptom affecting the user, the appearance of an existing symptom under conditions previously not associated with the existing symptom (e.g., the user is experiencing FOG at a time of day when they had previously not experienced it), or any suitable characteristic of a change in the user's symptoms. In some embodiments, the dosing control module 225 may apply the modification determined by the machine-learned model using the dosing 202. For example, the determined modification includes a change to the titration timing and dosage of levodopa, which the dosing control module 225 may implement by controlling a portable pump that administers levodopa or a similar stimulus to the user.

Machine learning models of the symptom intervention system 220 may use various machine learning techniques such as linear support vector machine (linear SVM), boosting for other algorithms (e.g., AdaBoost), neural networks, logistic regression, naïve Bayes, memory-based learning, random forests, bagged trees, decision trees, boosted trees, boosted stumps, a supervised or unsupervised learning algorithm, or any suitable combination thereof. The machine learning models may have access to a broader set of features on which to train. For example, the models may use physiological simulation as a component for identifying an onset of a symptom.

Alternatively, the models described herein may be a statistical model generated based on previously measured activity data and corresponding symptom onset identified. The statistical model may be configured to identify an onset of a symptom that is most likely to correspond to measured activity data. The models described herein may also be a rules-based decision model that identifies an onset of a symptom based on a test of various rules or conditions such as whether measured movement signals of the activity data deviates from an expected movement profile by over a threshold deviation, if the user is at a particular location or not, or any other suitable test for identifying an onset of a symptom based on evaluable conditions.

Although the symptom intervention system 220 is depicted as being a component of the symptom intervention assembly 110, the remote symptom intervention system 120 may provide the same or similar functionality such that the processing burden is shifted from the MCU 205 to processors local to the remote server hosting the remote symptom intervention system 120. The data captured by the sensors 201 may be communicated via the communications circuitry 204 to the remote symptom intervention system 120. For example, kinetic signals measured by the IMU sensors of the sensors 201 are stored in a Secure Digital (SD) memory card at a wearable device of the symptom intervention assembly 110 (e.g., components of the assembly 110 integrated into a knee wrap). The symptom intervention system 220 can upload data from the SD card to a remote database (e.g., the database 130), and the remote symptom intervention system 120 accesses the database 130 to identify an onset of a symptom and provide actuation instructions to the dosing 202 over the network 160. The remote symptom intervention system 120 may be hosted on a computing device such as a smartphone or a tablet, where the computing device can be communicatively coupled to the symptom intervention assembly 110 via the network 160.

Figure 3:
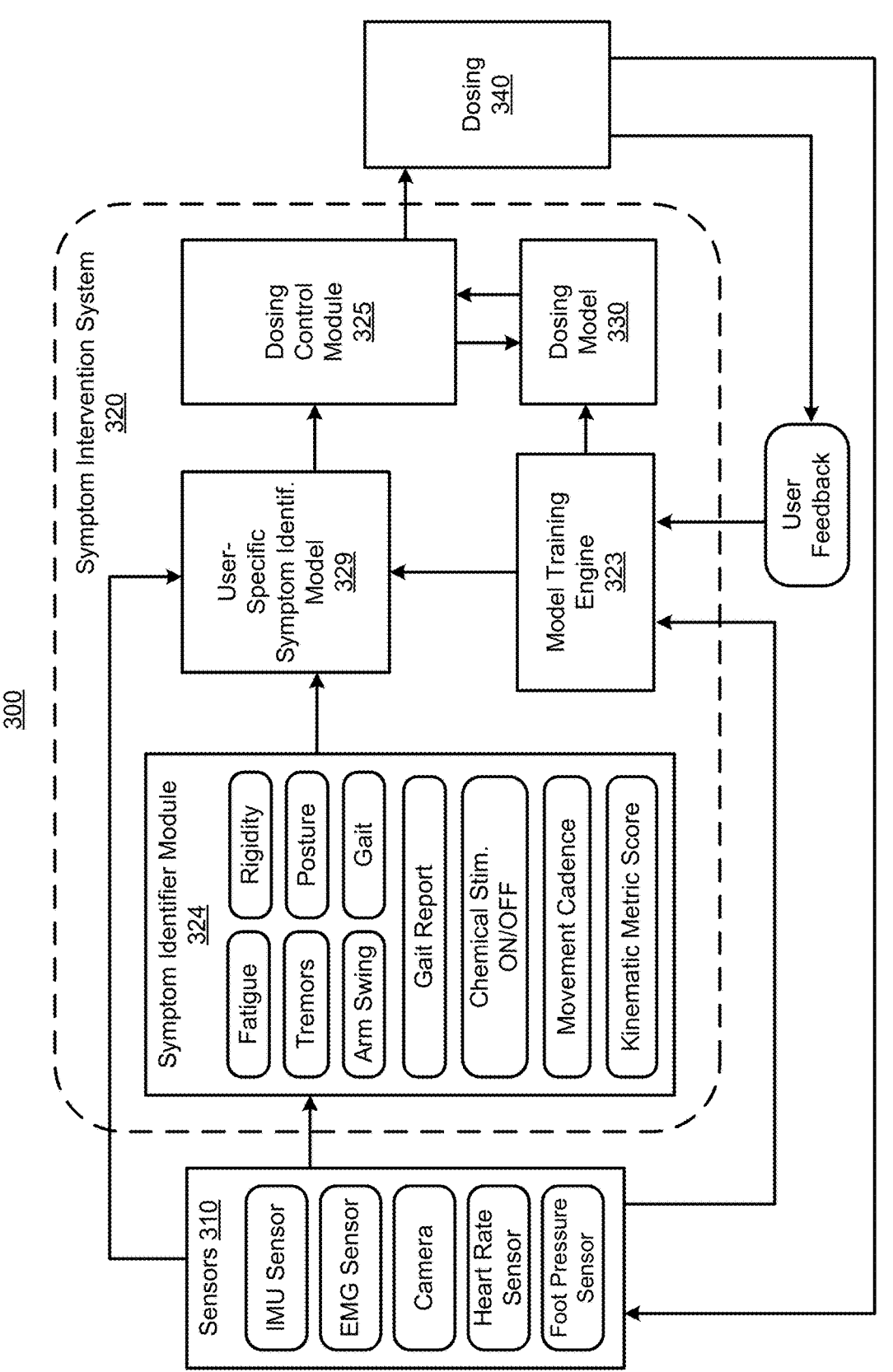
FIG. 3 is a block diagram of a feedback loop for optimizing symptom intervention by a symptom intervention assembly, in accordance with at least one embodiment.

FIG. 3 is a block diagram of a feedback loop 300 for optimizing symptom intervention by a symptom intervention assembly, in accordance with at least one embodiment. The feedback loop 300 is a closed-loop system that minimizes a difference between user movement assisted by the symptom intervention assembly and a target movement (e.g., a neurotypical movement). The feedback loop 300 may be performed by a symptom intervention system 320 of a symptom intervention assembly. For example, the symptom intervention system 320 monitors activity data, determines an actuation for symptom intervention based on the monitored activity data, monitors activity data capturing the user's movement assisted by applying the determined actuation (i.e., the monitored data serves as feedback), and adjusts a subsequently applied actuation based on the feedback. The feedback loop includes sensors 310, the symptom intervention system 320, and dosing 340. The symptom intervention system 320 may be the same or similar to the symptom intervention system 220 of FIG. 2. The system 320 includes a symptom identifier module 324, a user-specific symptom identification model 329, a dosing model 330, a model training engine 323, and a dosing control module 325. The feedback loop 300 may have alternative configurations than shown in FIG. 3, including different, fewer, or additional components.

The optimization of symptom intervention may begin with an initial application of actuation, which is determined by the symptom intervention system 320 using activity data monitored through the sensors 310. The sensors 310 measure activity data such as IMU signals, EMG signals, image data, heart rate, and foot pressure signals. The symptom identifier module 324 may determine characteristics of fatigue, tremors, arm swing, movement rigidity, a posture or change therein, or a gait. The module 324 may also determine "on" and "off" periods of a chemical stimulus, a movement cadence, kinematic metric score, or a gait report based on the measured activity data from the sensors 310. The symptom identifier module 324 may apply the user-specific identification model 329 to one or more of the measured activity data from the sensors 310 or derived activity data from the module 324. The user-specific identification model 329 and the dosing model 330 may be a machine-learned model trained by the model training engine 323. The model 329 can output a confidence score for the identification of an onset of a symptom, and in response to the confidence score meeting or exceeding a threshold confidence score, the symptom identifier module 324 may trigger the dosing control module 325 to determine an actuation instruction. The module 325 may use the dosing module 330 to determine an actuation instruction corresponding to the identified symptom. A symptom intervention system's determination of an actuation instruction for symptom intervention based on activity data is described in further detail in the description of FIG. 2.

The dosing control module 325 may be triggered by the symptom identifier module 324 after the module 324 determines that a symptom onset is occurring or will occur soon (e.g., after a time window, such as the "on" period of a chemical stimulus, passes). The dosing control module 325 uses the dosing model 330 to determine an actuation instruction based on the identified symptom onset, and provides the actuation instruction to the dosing 340. The output of actuators 340, as depicted in FIG. 3, is the user's movement as assisted by the actuation instruction. For example, the output of the dosing 340 could be a user's gait with the assistance of neuromodulation specified by the actuation instruction determined by the dosing control module 325. In another example, the output of the dosing 340 could be a user's still hands (i.e., lacking tremors) after the user's body has metabolized a modified dose of levodopa, where the modification is determined by the module 325 and applied by the dosing 340. The assisted movement may be monitored by the sensors 310, as depicted by the arrow connecting the dosing 340 to the sensors 310. The monitored assisted movement may be used as feedback to retrain the user-specific symptom identification model 329. The input of this feedback is depicted as an arrow between the sensors 310 and the model training engine 323. The user may also provide feedback of the assisted movement, which is provided to the symptom intervention system 320. For example, a user provides an approval rating of the assisted movement using a GUI generated on a user device that is communicatively coupled to the symptom intervention assembly and thus, to the symptom intervention system 320. The user feedback is used by the model training engine 323 of the symptom intervention system 320 to retrain the model 329.

The feedback is used to retrain the user-specific symptom identification model 329. The model training engine 323 may access the actuation instruction associated with the feedback received and score the applied actuation instruction based on the level of approval of the symptom intervention or assisted movement. The engine 323 may access the instruction from the dosing control module 325 as the instruction is determined or from a database storing previously applied actuation instructions (e.g., the actuation instruction database 221). The level of approval may be proportional to an amount by which an assisted movement deviates from a target movement, and the score may be proportional to the level of approval. Using the score, the model training engine 323 may create a training set of labeled data. Activity data can be labeled with an actuation instruction depending on the determined score. For example, if the score of the assisted movement is low due to low level of approval, the model training engine 323 may create a negative sample using the applied actuation as a label to the measured movement that resulted in the unsatisfactory actuation to be applied. In another example, if the score of the stimulated movement is high due to a high level of approval, the model training engine 323 may similarly create a positive sample. The model training engine 323 can use the positive and negative samples to re-train the user-specific symptom identification model 329 to refine the symptom intervention based on the user's body and behavior. Accordingly, feedback from monitored assisted movement or provided by the user through an interface allows the symptom intervention system to personalize and optimize the determined actuation and symptom intervention to the user.

FIG. 4 shows a configuration 400 of symptom intervention assembly components on or near a user's body, in accordance with at least one embodiment. The configuration 400 includes sensors to monitor activity data such as movement sensors 410-413, pressure sensors 420 and 421, and a camera 440. The configuration 400 includes actuators to intervene with symptoms of the user's physical condition such as neuromodulation electrodes 450 and a stimulation titration 460.

The symptom intervention assembly (e.g., the assembly 110 of FIGS. 1 and 2) monitors a user's movement through the movement sensors 410-413, which may include IMUs and EMG sensors located at the user's limbs. For example, movement sensors 410 and 411 are IMUs embedded within gloves worn by the user and provide movement signals indicative of the user's arm swings during a gait cycle (e.g., tracking the reduced arm swing of Parkinson's patients). The movement sensors 412 and 413 may be IMUs embedded within leggings worn by the user and provide movement signals indicative of the user's gait (e.g., tracking the symmetry of left and right leg steps). The pressure sensors 420 and 421 may be foot pressure sensors embedded within socks or the soles of shoes and provide pressure signals indicative of the user's gait (e.g., a frequency of steps or the strength of the step).

The camera 440 may be a camera installed within the user's home or at a medical professional's office to capture images or videos of the user's movement or changes in posture. The camera 440 may provide the captured data to a processor of the symptom intervention assembly (e.g., the MCU 205) for the symptom intervention system to perform image processing on the captured data. The captured data may depict movements of a gait like a toe-off or mid-swing or a user's posture. A symptom identifier module of the symptom intervention system may identify a symptom of a physical condition, such as a change in the user's posture (e.g., stooped shoulders of a user having Parkinson's disease), from the captured data.

The symptom intervention assembly components depicted in configuration 400 include actuators in both the neuromodulation electrodes 450 and the stimulus titration 460. The neuromodulation electrodes 450 are located at the user's brain and may be communicatively coupled to a controller that is implanted within the user. This controller may host the symptom intervention system or be communicatively coupled to the symptom intervention system such that it may receive actuation instructions from a dosing control module of the system. For example, the dosing control module determines to hyperpolarize neurons at the user's brain to heighten the relaxing of the user's muscles (e.g., to reduce rigidity in the user's arms or legs due to Parkinson's disease) and determines one or more electrodes of the neuromodulation electrodes 450 to serve as anodes to stimulate the muscle relaxation.

The symptom intervention assembly may also intervene with symptoms of a user's physical conditions by modifying a chemical stimulus's administration. The stimulus titration 460 may include a delivery system for a chemical stimulus such as levodopa, baclofen, carbidopa, or any other automatically administrable chemical stimulus for treating a physical condition that affects a user's movement. In one example, a delivery system of the titration 460 includes a pump that provides the chemical stimulus to the user through a tube into the user's body. The pump may include communications circuitry that enables it to receive actuation instructions from a symptom intervention system and a processor execute the instructions. In some embodiments, the delivery system includes a processor that hosts the symptom intervention system. An example actuation instruction that the stimulus titration 460 may execute is to modify the dose of levodopa to be 10% less than the current dose or to be delivered a determined amount of time earlier than scheduled.

In some embodiments, the symptom intervention system determines one or more actuation types to apply depending on the symptom identified. As described in the description of the dosing control module 225 of FIG. 2, the system may determine actuation instructions according to a rules-based system where an identified symptom or characteristic of the identified symptom corresponds to one or more actuation instructions. For example, the symptom intervention system may determine to activate both the neuromodulation electrodes 450 and the stimulus titration 460 in response to detecting a user's quality of gait has decreased to a predetermined quality (e.g., the kinetic signals deviate, on average, from a target signal beyond a threshold amplitude). Further, although not depicted, the configuration 400 may include actuators to apply biofeedback such as speakers, displays, or haptic mechanisms. Accordingly, a symptom intervention assembly, which may have the configuration 400, may help a user monitor for onsets of symptoms of their physical conditions in various manners and apply one or more actuation instructions to intervene with identified onsets.

User Interfaces for the Symptom Intervention System

FIG. 5 depicts a GUI for managing chemical stimulus administration modifications determined by a symptom intervention assembly, in accordance with at least one embodiment. The GUI may be displayed on a user device (e.g., the user device 150). The GUI includes a heading 510, a modification panel 520, and user feedback buttons 530. The GUI shows a determined modification to a user's current chemical stimulus administration (e.g., medical prescription of levodopa). A GUI module of a symptom intervention system (e.g., the GUI module 226) may retrieve the determined actuation instruction, as determined by the dosing control module 225, and provide it for display at the user device 150. The heading 510 indicates that the GUI is used to manage an actuation of chemical stimulus administration. As shown in the panel 520, the actuation instruction includes a proposed modification of the titration by −10% in dose amount and reducing the number of times the stimulus is taken by one time. A user of the symptom intervention assembly may select one of the user feedback buttons 530 to approve of the modification to their titration or deny the modification. In response to the user selecting one of the user feedback buttons 530, the user device 150 may provide the selection to the symptom intervention system to serve as instructions to either apply or not apply the modification through actuators or serve as feedback to retrain or update a model used to determine an onset of the symptom (e.g., the symptom identification models 228 or 229) or actuation instructions to apply (e.g., the dosing model 230).

FIG. 6 depicts a GUI for managing neuromodulation applied by a symptom intervention assembly, in accordance with at least one embodiment. The GUI may be displayed on a user device (e.g., the user device 150). The GUI includes a heading 610, an actuation summary panel 620, user feedback toggle 630, and an actuation termination button 640. The GUI shows a determined modification to a user's current chemical stimulus administration (e.g., medical prescription of levodopa). The GUI provides information about the actuation applied by the symptom intervention assembly and enables the user to manage the applied actuation. For example, the user can provide feedback of the actuation through the user feedback toggle 630 or stop the actuation through the button 640. The heading 610 indicates that the GUI is used to manage an actuation of neuromodulation. The panel 620 shows parameters of the neuromodulation such as a frequency, pulse width, and amplitude of the electrical signal. Further, the panel 620 provides information regarding the neuromodulation electrodes and their roles (e.g., anode, cathode, or disconnected), which may be indicated by different colors (or shading styles).

The user may provide direct or indirect feedback of the applied neuromodulation summarized in the panel 620. In one example, the user may use the toggle 630 to indicate a level of approval of the applied stimulation based on the comfort with or effectiveness of the neuromodulation. The level of approval may be on a sliding scale whose user-selected value is provided to the symptom intervention system by the user device 150 on which the GUI is displayed. This type of feedback may be direct feedback: user-provided information whose primary role is as feedback of the symptom intervention. In another example, the user may stop the actuation instruction being applied by the symptom intervention assembly using the button 640. This type of feedback may be indirect feedback: user-provided information whose primary role is to request a change in the operation of the symptom intervention assembly and whose secondary role is feedback of the symptom intervention.

The user-provided feedback through the GUIs depicted in FIGS. 5 and 6 can be stored in a user profile database (e.g., the user profile database 222) of the symptom intervention system. The user profile database 222 may store the user's chosen actuation modification and link the modification to the identified symptom or the user activity that predicated the applied actuation such that subsequent interventions are optimized to the user's modification (e.g., the actuation instruction is not applied for the identified symptom going forward).

Processes for Movement Assistance Using the Symptom Intervention System

Figure 7:
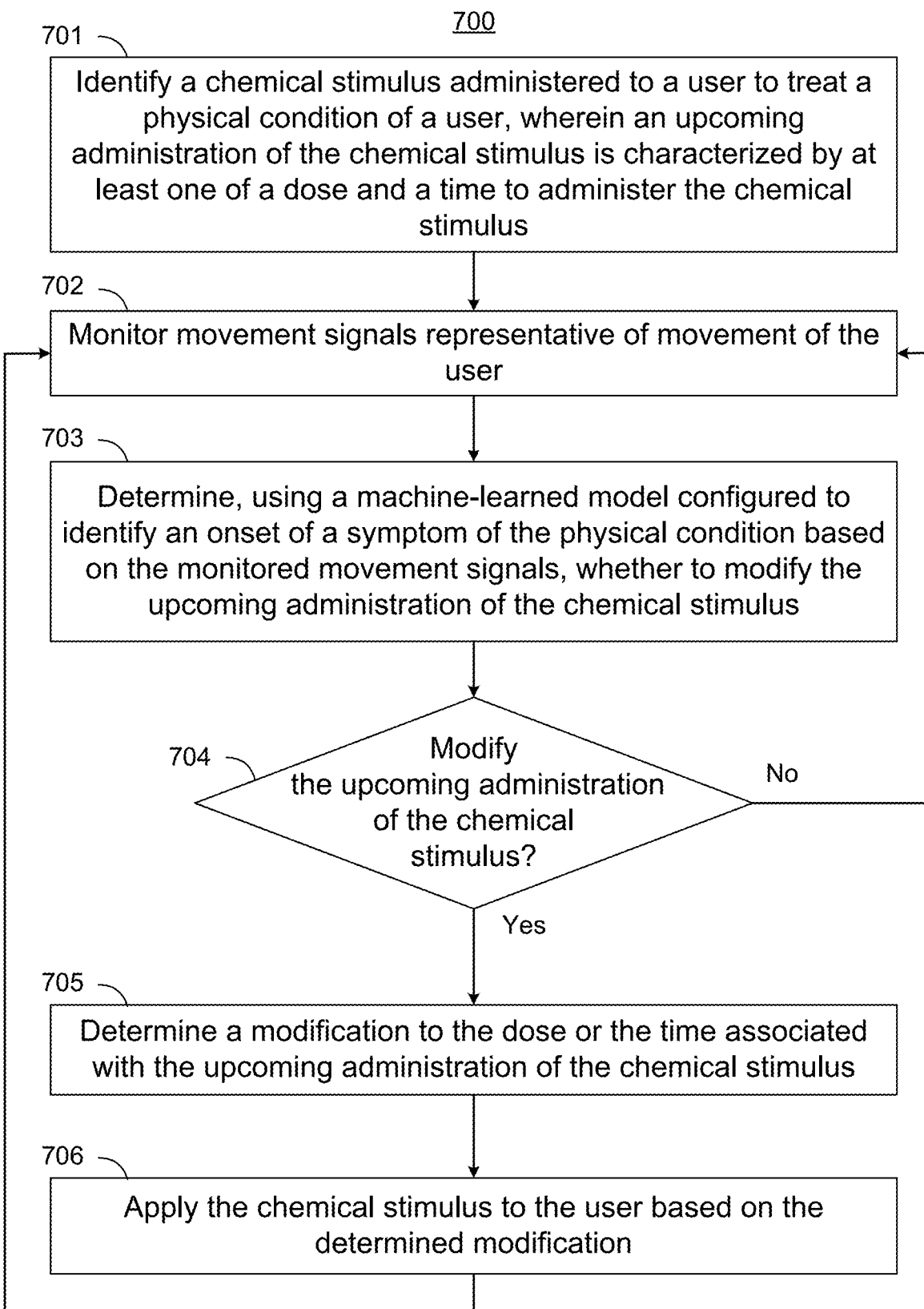
FIG. 7 is a flowchart illustrating a process for determining a modification to an upcoming administration of a chemical stimulus, in accordance with at least one embodiment.

FIG. 7 is a flowchart illustrating a process 700 for determining a modification to an upcoming administration of a chemical stimulus, in accordance with at least one embodiment. The symptom intervention system 220 can perform operations of the process 700 in parallel or in different orders, or perform different steps. For example, the symptom intervention system 220 may monitor 702 movement signals while identifying 701 a chemical stimulus. In another example, the system 220 can also monitor movement signals after the chemical stimulus is applied such that the process 700 may include a feedback loop to adjust subsequent administration modifications based on the applied stimulus. In this way, the process 700 may adjust and optimize the stimulus administration to the user's movements.

The symptom intervention system 220 identifies 701 a chemical stimulus administered to a user to treat a physical condition of a user, wherein an upcoming administration of the chemical stimulus is characterized by at least one of a dose and a time to administer the chemical stimulus. For example, the symptom identifier module 224 or the dosing control module 225 may query the user profile database 222 to identify 701 that the user is taking levodopa, the dose of levodopa being taken, and at which times during the day that the doses are taken. The levodopa may be titrated the user throughout the day. For example, a larger dose may be administered in the morning and gradually smaller doses are administered to the user every couple of hours until some time in the evening. The system 220 may determine the current time of day and identify that, based on the current time of day, an upcoming administration of levodopa is to be administered at a dose of 50 mg at 14:00. The system 220 may notify the user (e.g., through the user device 150) at 14:00 to take a pill for levodopa. Alternatively, the administration may be automated using a pump and a gel form of levodopa.

The symptom intervention system 220 monitors 702 movement signals representative of movement of the user. The symptom identifier module 224 may receive kinematic signals measured using IMUs of the sensors 201, where the IMUs are located at the user's legs such that the received kinematic signals reflect the user's gait. The kinematic signals may show that the acceleration of one of the user's legs during a gait cycle is decreasing, which may indicate an upcoming onset a symptom of Parkinson's disease (e.g., imbalanced gait or shuffling). These kinematic signals may also indicate that the "on" period of the last dose of levodopa taken is reaching its end, and that an "off" period is soon to set in.

The symptom intervention system 220 determines 703, using a machine-learned model configured to identify an onset of a symptom of the physical condition based on the monitored movement signals, whether to modify the upcoming administration of the chemical stimulus. The symptom identifier module 224 may apply the user-specific symptom identification model 229 to the monitored movement signals. The model 229 may be trained using kinematic signals representing the user's gait similar to the monitored signals (e.g., using IMUs located at the same location as the IMUs monitoring the user), where the kinematic signals represent the gait when the user is experiencing, or soon to experience, a symptom and is labeled with the symptom. The model training engine 227 may perform this training. The output of the machine-learned model 229 may be an identification of the symptom (e.g., an imbalanced gait) and a confidence of the identification. For example, the model 229 determines with 70% confidence that the monitored 702 movement signals indicate an onset of an imbalanced gait.

The symptom intervention system 220 determines 704 whether to modify the upcoming administration of the chemical stimulus. The symptom identifier module 224 may use a confidence score associated with the machine-learned model's identification of the onset of the symptom to determine 704 whether to modify the upcoming administration. For example, the symptom identifier module 224 uses a predefined threshold confidence score of 70%, where a confidence score meeting or exceeding that threshold warrants modification to an upcoming administration. An identification by the machine-learned model 229 of an onset of imbalanced gait with a 70% confidence may thus cause the symptom identifier module 224 to trigger the dosing control module 225 to determine a modification. Otherwise, if the confidence score does not meet or exceed the threshold confidence score, the process 700 may return monitoring 702 movement signals representative of movement of the user. These subsequently monitored movement signals can be used to determine whether an onset of a symptom is likely to occur and whether an upcoming administration should be modified.

The symptom intervention system 220 determines 705 a modification to the dose or the time associated with the upcoming administration of the chemical stimulus. The dosing control module 225 may determine to modify a dose of the upcoming administration based on the monitored 702 movement signals. For example, the module 225 may compare the gait movement characterized by the monitored signals to a target movement, which may be characterized by previously measured kinematic signals, and determine a measure of the deviation from the target movement. Using this deviation, the module 225 may determine an amount by which the dose should increase or decrease. For example, the module 225 may access historical records of dose modifications (e.g., as determined manually by medical professionals or automatically by the symptom intervention assembly) to determine a recommended modification that is similar to previous modifications for similar deviations from a target movement.

The dosing control module 225 may determine to modify a time associated with the upcoming administration based on the monitored 702 movement signals. For example, the module 225 may use "on" and "off" periods of a chemical stimulus to determine how the time should be modified. The module 225 may determine a time at which an "off" time duration of levodopa will begin. The symptom intervention system may access historical records of kinematic signals mapped to corresponding times during "on" or "off" periods of levodopa, and compare the monitored movement signals to the historical records to determine the time at which the "off" period will begin. The dosing control module 225 may identify a stimulus metabolism period that indicates a time period between the intake of a chemical stimulus and a peak efficacy of the chemical stimulus. This stimulus metabolism may be manually provided (e.g., by a medical professional) or estimated by the symptom intervention system based on hormone activities within the user's body. The module 225 may update the administration time of levodopa to be earlier than the time at which the "off" period will begin by the stimulus metabolism period. For example, if the original upcoming time to take levodopa was 14:00, the module 225 determines that an "off" period will start at 13:55 and the stimulus metabolism period is 15 minutes long, the module 225 may automatically administer, or notify the user to take their next dose of levodopa, at 13:40 instead of at 14:00.

The symptom intervention system 220 applies 706 the chemical stimulus to the user based on the determined modification. The dosing control module 225 may provide actuation instructions to the dosing 202 to apply 706 the chemical stimulus at the modified time or dose. For example, the module 225 may provide actuation instructions that a levodopa pump administer the next dose of levodopa at 13:40 instead of at 14:00, thus applying 706 the levodopa to the user based on the determined administration time modification. The process 700 may return to monitoring 702 movement signals to continue optimizing symptom intervention over time.

FIG. 8 is a flowchart illustrating a process 800 for applying neuromodulation, in accordance with at least one embodiment. The symptom intervention system 220 monitors 801 movement signals representative of movement of a user. The symptom identifier module 224 may receive kinematic signals measured using IMUs and EMG signals measured using EMG sensors of the sensors 201. The IMUs and EMG sensors can be located at the user's legs such that the received kinematic and EMG signals reflect the user's gait or intention to step through their gait. The monitored signals may show signs of a physical condition's symptoms in the user's gait. For example, fatigue is a symptom of Parkinson's, and may be caused by akinesia (i.e., difficulty starting a movement) or extra strain on muscles caused by other symptoms in Parkinson's disease such as muscle stiffness or tremors. The monitored 801 movement may indicate the onset of fatigue in a slowness or weakness in movement through the gait. For example, IMU signals show that the acceleration of one of the user's legs during a gait cycle is decreasing. The EMG signals may show the frequency of electroactivity is decreasing. The symptom identifier module 224 may identify both the decrease in acceleration and frequency of electroactivity.

The symptom intervention system 220 determines 802, using a machine-learned model configured to identify an onset of a symptom of a physical condition based the monitored movement signals, whether to modify parameters of neuromodulation symptom intervention. The system 220 may determine that the user is exhibiting a particular symptom of the symptoms of the physical condition, and in response to determining the particular symptom is being exhibited, determine to modify neuromodulation parameters. A physical condition may have many symptoms. For example, Parkinson's disease symptoms include tremors, FOG, imbalanced gait, shuffling or slowed gait, fatigue, bradykinesia, and other symptoms related or unrelated to movement. The symptom intervention system 220 may use a machine-learned model to identify the onset of one or more of these symptoms, the number of which may depend on the way a machine-learned model is trained or the number of trained machine-learned models maintained by the symptom intervention system 220. For example, the system 220 may train and apply a machine-learned model for respective Parkinson's disease symptoms, where each model can be trained on activity data that is labeled with the corresponding symptom. The symptom identifier module 224 may apply the user-specific symptom identification model to the monitored 801 EMG and IMU signals to identify that an onset of fatigue is occurring. In another example, the symptom identifier module 224 may apply the general symptom identification model 228 to IMU signals monitored 801 at the user's hands to identify that an onset of a tremor is occurring.

The symptom intervention system 220 can determine whether the particular symptom is a first symptom or a second symptom of the user's physical condition symptoms. A machine-learned model may output a confidence score associated with the identification of an onset of a symptom, and the symptom identifier module 224 may use the confidence score to determine whether the identified onset is indeed an onset of the symptom. For example, the symptom identifier module 224 compares a confidence score associated with the identification of the onset of fatigue by the user-specific symptom identification model 229 with a threshold confidence score to determine that the user is, with a sufficiently high likelihood, experiencing the onset of fatigue. The module 224 may also apply another machine-learned model to the activity data, where the other machine-learned model is trained to identify the onset of tremors, and reinforce, based on a confidence score output by the other model, its determination that the user is experiencing the onset of fatigue rather than the onset of a tremor. In a second example, the symptom identifier module 224 may similarly determine that the monitored 801 IMU signals at the user's hands indicate the onset of a tremor rather than fatigue. In these examples, the first symptom identifiable by the module 224 is fatigue while the second symptom is a tremor.

The symptom intervention system 220 determines 803 a modification to neuromodulation parameters, which can include at least one of a frequency, pulse width, amplitude, polarization, or duration of an electrical signal. The system 220 can modify parameters to depolarize a first plurality of neurons of the user if the system 220 determines the particular symptom exhibited is a first symptom. Following an earlier example, a first symptom of the user's condition is fatigue while a second symptom is a tremor. Depolarizing a user's particular neuron or group of neurons may cause a corresponding muscle group to contract. Assisted contraction of the muscle may be helpful to perform motions such as walking. Accordingly, when the symptom identifier module 224 determines that the user is or will experience the onset of fatigue that affects their gait, the module 224 triggers the dosing control module 225 to determine an appropriate actuation instruction to stimulate neuromodulation electrodes and contract muscles for the user's gait.

The dosing control module 225 may determine the appropriate actuation instruction based on monitored EMG signals and rules mapping a configuration of neuromodulation electrodes to the stimulation of a corresponding muscle group. Examples of using EMG signals to determine electrical stimulation (e.g., FES) may be found in U.S. patent application Ser. Nos. 17/113,058 and 17/113,059, filed Dec. 6, 2020, which are incorporated herein by reference. For example, the module 225 may determine from monitored EMG signals that the user is intending to perform a toe-off in the gait cycle and in response, the module 225 uses a mapping of toe-off to a particular configuration of neuromodulation electrodes to determine which neuromodulation electrodes are to be anodes, cathodes, or disconnected and the parameters (e.g., frequency, pulse width, and amplitude) of the neuromodulation signal applied through the determined electrode configuration. In particular, the module 225 may determine which of multiple configurable electrodes should operate as a cathode to depolarize the appropriate neurons. The module 225 may determine the appropriate neuromodulation stimulation for each movement within a gait cycle, thus helping the user contract the appropriate muscles while they walk.

The symptom intervention system 220 can determine 803 a modification to neuromodulation parameters that hyperpolarizes a second plurality of neurons of the user if the system 220 determines the particular symptom exhibited is the second symptom. Hyperpolarizing a user's particular neuron or group of neurons may cause a corresponding muscle group to relax or achieve heightened relaxation. Assisted relaxation of the muscle may be helpful to reduce or prevent tremors, which are characterized by involuntary contractions of muscles. Following an earlier example, a first symptom of the user's condition is fatigue while a second symptom is a tremor. Accordingly, when the symptom identifier module 224 determines that the user is or will experience the onset of a tremor, the module 224 triggers the dosing control module 225 to determine an appropriate actuation instruction to stimulate neuromodulation electrodes and relax muscles to control the tremor. For example, the module 225 may determine from monitored IMU signals that the user has tremors of a particular severity (e.g., frequency or magnitude of the tremors) and in response, the module 225 uses a mapping of the severity to a particular configuration of neuromodulation electrodes and the parameters of the neuromodulation signal applied through the determined electrode configuration. In particular, the module 225 may determine which of multiple configurable electrodes should operate as an anode to hyperpolarize the appropriate neurons.

The symptom intervention system 220 may apply 804 neuromodulation intervention to the user based on the determined modification. For example, the system 220 applies an electrical signal characterized by the modified neuromodulation parameters to electrodes of the dosing 202. The electrodes may be proximate to neurons of the user (e.g., at the brain or a muscle group such as a shank). The process 800 may return to monitoring 801 movement signals to dynamically optimize the application of neuromodulation (e.g., when and how) to the user's movement.

Experimental Findings

Figure 9:
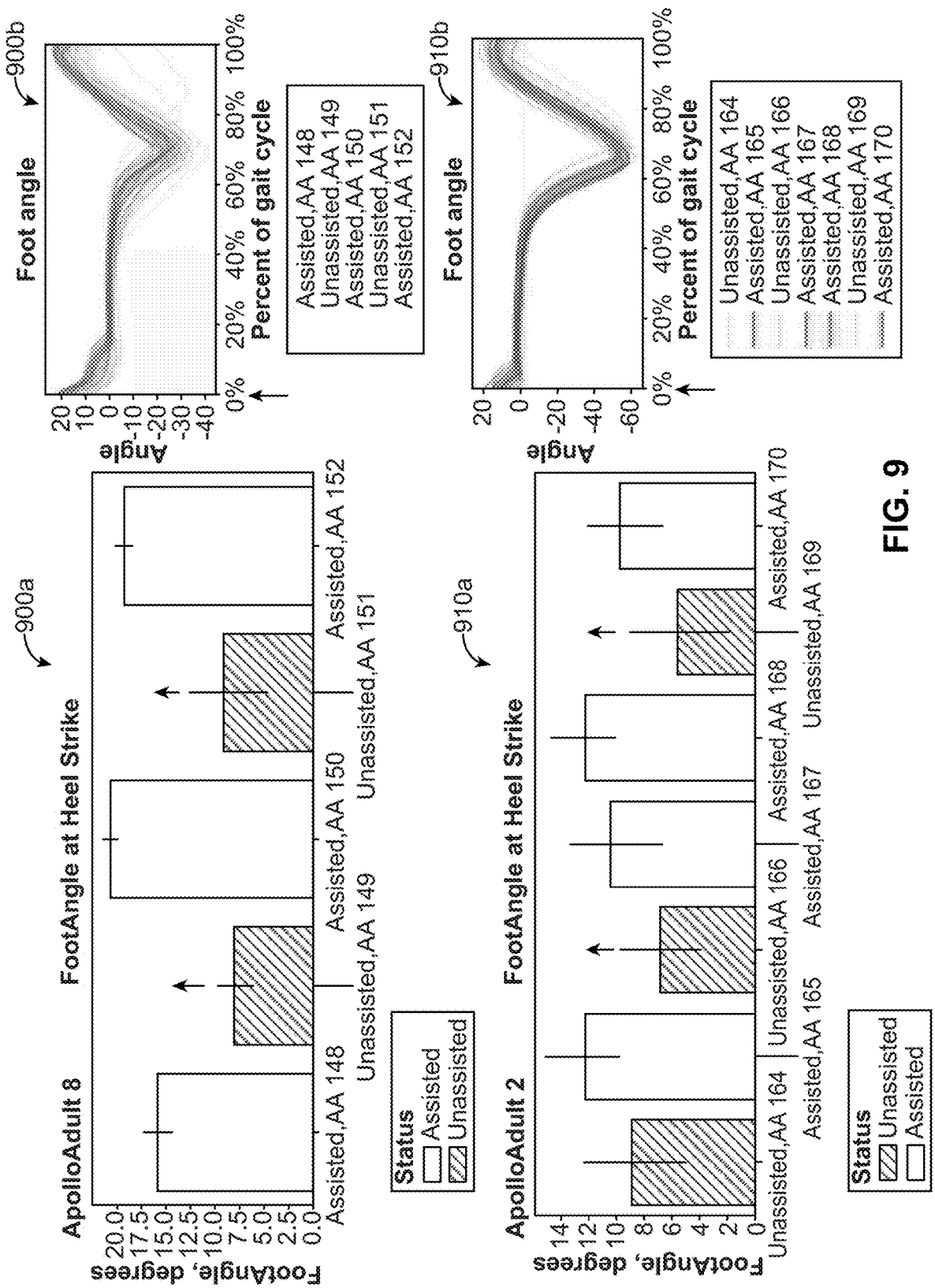
FIG. 9 shows experimental findings of the intervention of drop foot in two adult users by the symptom intervention assembly described herein.

FIG. 9 shows experimental findings 900 and 910 of the intervention of drop foot in two adult users by the symptom intervention assembly described herein. Drop foot may primarily be a symptom of users who have previously suffered from a stroke, but can also affect users having CP or MS. Drop foot occurs during a gait where the foot does not return to zero degrees (i.e., the sole of the foot is flat or substantially parallel to a level ground), which may cause tripping and compromise their gait. A symptom intervention assembly measured the drop foot through kinematic signals captured at sensors coupled to the user's foot (e.g., IMUs embedded in a user's shoe). The assembly can determine the onset of the drop foot based on the measured movement signals and determined to apply FES stimulation to intervene with the drop foot. The resulting movement with assistance from the FES stimulation is shown in the findings 900 and 910 along with the measured movement without assistance from the FES stimulation. The findings 900 and 910 show that the assembly improved metrics that measure the quality of a gait such as foot angle at heel strike, loading response time (i.e., the time taken for a foot to transition from heel strike to flat foot), and average dorsiflexion in a swing. The dorsiflexion can be the direct causal result of the FES stimulation (e.g., causing the foot to lift). In the graphs showing the adult users' foot angles at heel strike, the FES actuation provided by the symptom intervention assembly was able to stimulate the foot to lift in its dorsiflexion and increase the foot angle at heel strike. As shown in the graphs of the adult users' foot angle over a full gait cycle, the FES actuation is able to produce a gait that does not drop (i.e., front of feet pointing downward) with an angle magnitude as large as a gait without assistance. Further, the FES actuation is able to produce a gait that can return and stay at zero degrees (e.g., at 20% through approximately 50% of the gait cycle) more consistently than the unassisted gait.

FIG. 10 shows experimental findings 1000*a* and 1000*b* of knee kinematics augmented with FES. The findings 1000*a* and 1000*b* were taken from a 10 year-old child with primarily unilateral spastic CP. Her movements were monitored with and without FES. The sensors and actuators of a symptom intervention assembly were positioned at each of her legs and the sensors measured kinematic signals from her gait cycle. Her right leg showed neurotypical movement while her left leg's movement was impacted by CP. She experienced the CP symptom of crouch gait, which is characterized by a deeper bend in the knee when walking. A symptom intervention assembly was able to apply FES to intervene with the crouch gait, decreasing the joint angle in the left leg so that it more closely mirrored her right leg.

Graph 1000*a* shows her knee kinematics without FES applied. Kinematic signal 1001*a* of the graph 1000*a* shows her right knee's flexion angle exhibiting neurotypical movement. Kinematic signal 1002*a* of the graph 1000*a* shows her left knee's flexion angle exhibiting neuro-atypical movement. Graph 1000*b* shows her knee kinematics with FES applied. Kinematic signal 1001*b* of the graph 1000*b* shows her right knee's flexion angle exhibiting neurotypical movement. Kinematic signal 1002*b* of the graph 1000*b* shows her left knee's flexion angle augmented by FES and exhibiting movement that more closely aligns with the neurotypical kinematic signal 1001*b* than with the neuro-atypical kinematic signal 1002*a*.

Figure 11:
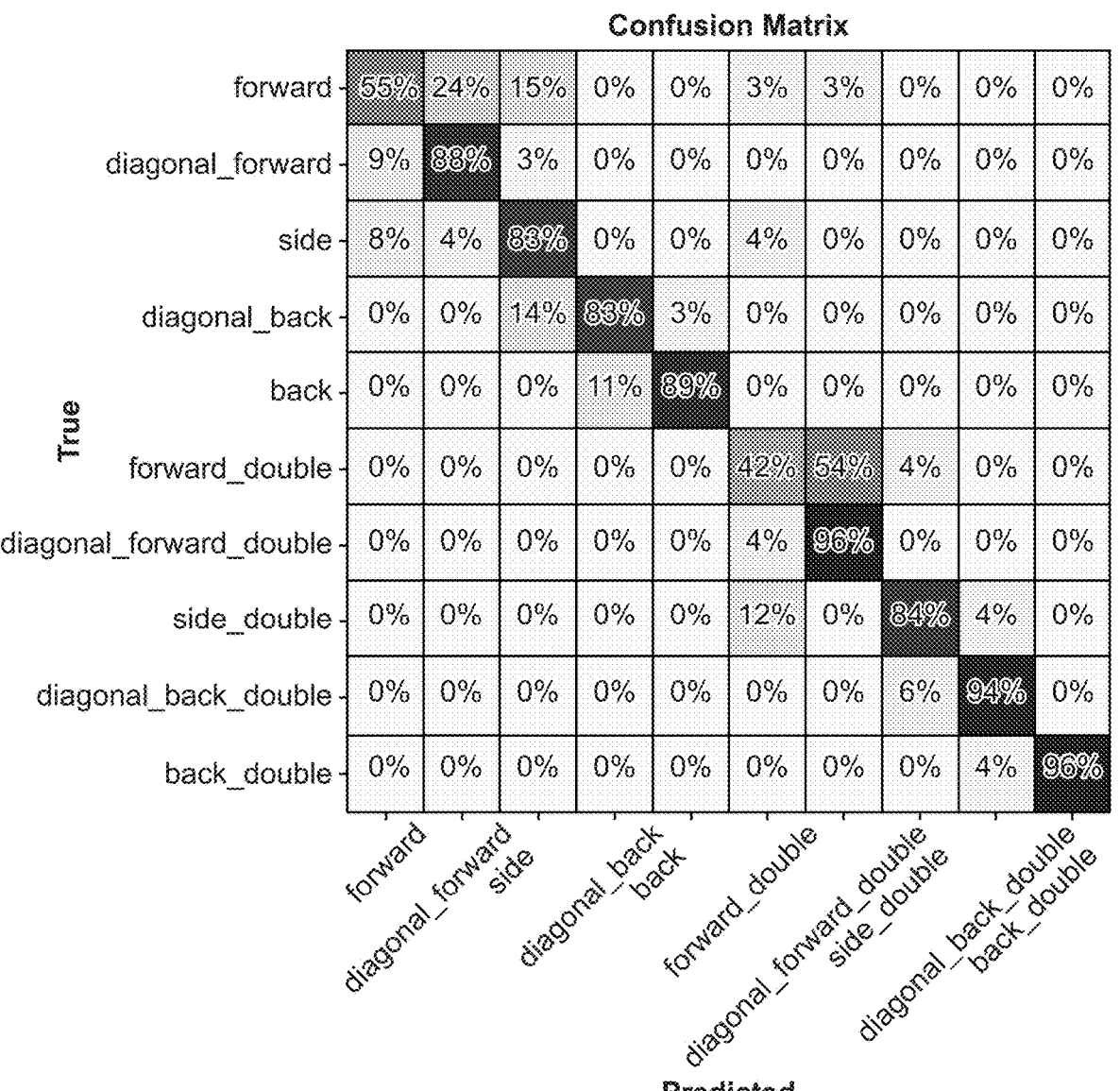
FIG. 11 shows an experimental finding of the movement prediction accuracy of the symptom intervention assembly.

FIG. 11 shows an experimental finding 1100 of the movement prediction accuracy of the symptom intervention assembly. Sensors of the symptom intervention assembly measured EMG signals representing the user's intention to move as the user took a step forward ("forward"), forward diagonally ("diagonal forward"), sideway ("side"), backward diagonally ("diagonal back"), backward ("back"), forward twice ("forward double"), forward diagonally twice ("diagonal forward double"), sideway twice ("side double"), backward diagonally twice ("diagonal back double"), and backward twice ("back double"). The confusion matrix shows a matrix of prediction accuracy values. The accuracy of a predicted movement against the true movement are listed in the cells of the confusion matrix. For example, the symptom intervention assembly accurately predicted a step forward diagonally twice with 96% accuracy, where the remaining 4% of the predictions were incorrectly predicted as a step forward twice. The shading in the confusion matrix corresponds to the level of accuracy, where darker shading indicates higher accuracy. The experimental finding 1100 shows that the symptom intervention assembly can predict movements from measured EMG signals with high accuracy.

FIG. 12 shows experimental findings 1200 and 1210 of the impact of fatigue upon muscle electroactivity. The symptom intervention assembly can monitor a user's EMG signals and determine a level of fatigue, which can be used to predict events (e.g., slowed or shuffling gait) resulting from the fatigue. The finding 1200 shows a frequency response of EMG signals measured at a user of the symptom intervention assembly when the user was rested and when the user was fatigued. A rested muscle has a high frequency response than a fatigued muscle. In particular, fast twitch muscles can be the first to tire, and EMG signals measured at those muscles shows a lower frequency content when those muscles become fatigued. The symptom intervention assembly can combine measured kinematics and EMG signals to perform event prediction. Further, EMG signals and fatigue may be metrics for determining if the user is experiencing an "on" or "off" period of a chemical stimulus.

Additional Considerations

The foregoing description of the embodiments has been presented for the purpose of illustration; it is not intended to be exhaustive or to limit the patent rights to the precise forms disclosed. Persons skilled in the relevant art can appreciate that many modifications and variations are possible in light of the above disclosure.

Some portions of the preceding detailed descriptions have been presented in terms of algorithms and symbolic representations of operations on data bits within a computer memory. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

The present disclosure also relates to an apparatus for performing the operations herein. This apparatus may be specially constructed for the intended purposes, or it may include a computer selectively activated or reconfigured by a computer program stored in the computer. Such a computer program may be stored in a computer readable storage medium, such as, but not limited to, any type of disk including CD-ROMs and magnetic-optical disks, read-only memories (ROMs), random access memories (RAMs), EPROMs, EEPROMs, magnetic or optical cards, or any type of media suitable for storing electronic instructions, each coupled to a computer system bus.

In addition, the present disclosure is not described with reference to any particular programming language. It will be appreciated that a variety of programming languages may be used to implement the teachings of the disclosure as described herein. Embodiments may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a non-transitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment. Where values are described as "approximate" or "substantially" (or their derivatives), such values should be construed as accurate +/–10% unless another meaning is apparent from the context. From example, "approximately ten" should be understood to mean "in a range from nine to eleven." As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present). In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

Finally, the language used in the specification has been principally selected for readability and instructional purposes, and it may not have been selected to delineate or circumscribe the patent rights. It is therefore intended that the scope of the patent rights be limited not by this detailed description, but rather by any claims that issue on an application based hereon. Accordingly, the disclosure of the embodiments is intended to be illustrative, but not limiting, of the scope of the patent rights, which is set forth in the following claims.

What is claimed is:

1. A method comprising:
monitoring a plurality of movement signals at a muscle group of a foot, a shank, or a thigh of a user, the movement signals representative of a phase in a gait cycle of the user;
determining, using a machine-learned model configured to identify an onset of a symptom of a physical condition based on the monitored plurality of movement signals, that the user is exhibiting the symptom of a plurality of symptoms of the physical condition, wherein the machine-learned model is trained using a first training set comprising historical activity data collected from sensors monitoring a plurality of users having the physical condition, the first training set being labeled with symptom onset events for said plurality of users and wherein the model is retrained by adjusting parameters of the model in response to a second training set comprising data representative of measured movement collected from the user, the second training set being labeled with symptom onset events detected for the user such that the machine-learned model is customized to the user;
based on a magnitude of the symptom exhibited by the user and characteristics of the user, identifying a neuromodulation operation comprising an electrical stimulation signal to mitigate the symptom; and
applying the identified neuromodulation operation to the user via a wearable neuromodulation system comprising a plurality of electrodes physically coupled to the user.

2. The method of claim 1, wherein applying the identified neuromodulation operation to the user via the wearable neuromodulation system comprises:

in response to determining that the symptom is a first symptom of the plurality of symptoms, depolarizing a first plurality of neurons of the user; and
in response to determining that the symptom is a second symptom of the plurality of symptoms, hyperpolarizing a second plurality of neurons of the user.

3. The method of claim 2, wherein depolarizing the first plurality of neurons comprises determining at least one of the plurality of electrodes to operate as a cathode.

4. The method of claim 2, wherein hyperpolarizing the second plurality of neurons comprises determining at least one of the plurality of electrodes to operate as an anode.

5. The method of claim 1, further comprising:
comparing the plurality of movement signals to a symptom profile, wherein the symptom profile is created using historical movement data representative of movement while a given user is experiencing the symptom without assistance from a chemical stimulus,
wherein applying the identified neuromodulation operation to the user via the wearable neuromodulation system comprises:
determining a plurality of electrical stimulation parameters based on the comparison of the plurality of movement signals to the symptom profile, the plurality of electrical stimulation parameters including a voltage, a pulse width, a polarity, or a frequency of the electrical stimulation signal; and
configuring the electrical stimulation signal to flow between a first electrode of the plurality of electrodes and a second electrode of the plurality of electrodes, wherein the first electrode is configured to operate as a cathode stimulating a first plurality of neurons.

6. The method of claim 1, further comprising:
determining a change in a frequency at which the onset of the symptom is identified, wherein applying the identified neuromodulation operation to the user via the wearable neuromodulation system comprises:
determining a plurality of electrical stimulation parameters of the electrical stimulation signal based on the change in the frequency; and
configuring the electrical stimulation signal to flow between a first electrode of the plurality of electrodes and a second electrode of the plurality of electrodes, wherein the first electrode is configured to operate as a cathode stimulating a first plurality of neurons.

7. The method of claim 1,
wherein the historical activity data includes at least one of historical movement signals, hormone activity, a previous administration of a chemical stimulus administered to the user to treat the physical condition, heart rate, or respiration rate; and
wherein the method further comprises labeling the historical activity data with a given symptom label representative of a corresponding symptom characterized by the historical activity data.

8. The method of claim 7, further comprising:
causing a client device to render a graphical user interface (GUI) comprising a user input field to stop the neuromodulation operation;
in response to receiving a user input at the user input field, modifying an association between the identified onset of the symptom of the physical condition and the monitored plurality of movement signals; and
retraining the machine-learned model using the modified association.

9. The method of claim 1, further comprising monitoring hormone activity of the user using a plurality of sensors configured to measure at least one of a level of a hormone or a level of a biomolecule regulated by the hormone, wherein the machine-learned model is configured to identify the onset of the symptom of the physical condition further based on the monitored hormone activity.

10. The method of claim 1, wherein determining, using the machine-learned model, that the user is exhibiting the symptom comprises:

generating a feature vector representative of the monitored plurality of movement signals and one or more of a hormone activity of the user, a previous administration of a chemical stimulus administered to the user to treat the physical condition, and motor intent data of the user;

applying the machine-learned model to the feature vector, wherein machine-learned model identifies the onset of the symptom with a confidence score as being associated with the feature vector; and in response to the confidence score exceeding a threshold confidence, determining that the user is exhibiting the symptom.

11. The method of claim 1, further comprising:

determining an "on" time duration of a previous administration of a chemical stimulus administered to the user to treat the physical condition, the "on" time duration starting at a first time to administer the chemical stimulus and ending at an occurrence of the symptom after the first time to administer the chemical stimulus, the first occurrence of the symptom identified using the machine-learned model;

determining an "off" time duration of the previous administration of the chemical stimulus, the "off" time duration starting at the first occurrence of the symptom and ending at a second time to administer the chemical stimulus after the first time; and wherein determining that the user is exhibiting the symptom of the plurality of symptoms of the physical condition is in response to determining that the "off" time duration is greater than the "on" time duration.

12. The method of claim 11, wherein the chemical stimulus is one of levodopa, carbidopa, or baclofen.

13. The method of claim 1, wherein the plurality of movement signals is a first plurality of movement signals, further comprising:

measuring a second plurality of movement signals at a first joint of the user;

measuring a third plurality of movement signals at a second joint of the user, the second joint symmetric about a sagittal plane to the first joint;

determining a first kinematic metric score based on a comparison of the second plurality of movement signals to the third plurality of movement signals, the first kinematic metric score indicative of a measure of symmetry of motion about a sagittal plane;

generating a baseline movement profile of the first joint using historical movement signals collected at the first joint; and determining a second kinematic metric score based on a comparison of the second plurality of movement signals to the baseline movement profile, the second kinematic metric score indicative of a measure of a variance from an expected movement, wherein the machine-learned model is configured to identify the onset of the symptom of the physical condition further based on at least one of the first kinematic metric score or the second kinematic metric score.

14. The method of claim 1, further comprising:

determining a movement frequency response of the plurality of movement signals, wherein the machine-learned model is configured to identify the onset of the symptom of the physical condition further based on the movement frequency response.

15. The method of claim 1, further comprising:

creating a baseline gait profile using historical movement signals measured at the muscle group; and determining a gait report score based on a comparison of the plurality of movement signals to the baseline gait profile, wherein the machine-learned model is configured to identify the onset of the symptom of the physical condition further based on the gait report score.

16. The method of claim 1, further comprising, in response to determining that the user is exhibiting one of the plurality of symptoms of the physical condition, providing a biofeedback to the user, the biofeedback including one or more of a sensory cue to promote a neurotypical movement in the user.

17. The method of claim 1, wherein the physical condition is Parkinson's disease and wherein the symptom is one of a gait freeze or tremor.

18. A system comprising a non-transitory computer-readable storage medium storing instructions for execution and a hardware processor configured to execute the instructions, the instructions, when executed, cause the hardware processor to perform steps comprising:

monitoring a plurality of movement signals at a muscle group of a foot, a shank, or a thigh of a user, the movement signals representative of a phase in a gait cycle of the user;

determining, using a machine-learned model configured to identify an onset of a symptom of a physical condition based on the monitored plurality of movement signals, that the user is exhibiting the symptom of a plurality of symptoms of the physical condition, wherein the machine-learned model is trained using a first training set comprising historical activity data collected from sensors monitoring a plurality of users having the physical condition, the first training set being labeled with symptom onset events for said plurality of users and wherein the model is retrained by adjusting parameters of the model in response to a second training set comprising data representative of measured movement collected from the user, the second training set being labeled with symptom onset events detected for the user such that the machine-learned model is customized to the user;

based on a magnitude of the symptom exhibited by the user and characteristics of the user, identifying a neuromodulation operation comprising an electrical stimulation signal to mitigate the symptom; and applying the identified neuromodulation operation to the user via a wearable neuromodulation system comprising a plurality of electrodes physically coupled to the user.

19. A non-transitory computer readable storage medium storing executable instructions that, when executed by one or more processors, cause the one or more processors to perform steps comprising:

monitoring a plurality of movement signals at a muscle group of a foot, a shank, or a thigh of a user, the movement signals representative of a phase in a gait cycle of the user;

determining, using a machine-learned model configured to identify an onset of a symptom of a physical condition based on the monitored plurality of movement signals, that the user is exhibiting the symptom of a plurality of symptoms of the physical condition, wherein the machine-learned model is trained using a first training set comprising historical activity data collected from sensors monitoring a plurality of users having the physical condition, the first training set being labeled with symptom onset events for said plurality of users and wherein the model is retrained by adjusting parameters of the model in response to a second training set comprising data representative of measured movement collected from the user, the second training set being labeled with symptom onset events detected for the user such that the machine-learned model is customized to the user;

based on a magnitude of the symptom exhibited by the user and characteristics of the user, identifying a neuromodulation operation comprising an electrical stimulation signal to mitigate the symptom; and applying the identified neuromodulation operation to the user via a wearable neuromodulation system comprising a plurality of electrodes physically coupled to the user.

\* \* \* \* \*